United States Patent
Kim et al.

(10) Patent No.: US 10,664,049 B2
(45) Date of Patent: May 26, 2020

(54) SYSTEMS AND METHODS FOR GAZE TRACKING

(71) Applicant: NVIDIA Corporation, Santa Clara, CA (US)

(72) Inventors: Joohwan Kim, Berkeley, CA (US); Ward Lopes, Redwood City, CA (US); David Patrick Luebke, Charlottesville, VA (US); Chengyuan Lin, West Lafayette, IN (US)

(73) Assignee: NVIDIA Corporation, Santa Clara, CA (US)

( * ) Notice: Subject to any disclaimer, the term of this patent is extended or adjusted under 35 U.S.C. 154(b) by 97 days.

(21) Appl. No.: 15/809,849

(22) Filed: Nov. 10, 2017

(65) Prior Publication Data

US 2018/0164880 A1  Jun. 14, 2018

Related U.S. Application Data

(60) Provisional application No. 62/432,454, filed on Dec. 9, 2016.

(51) Int. Cl.
*G06F 3/01* (2006.01)
*A61B 3/113* (2006.01)
(Continued)

(52) U.S. Cl.
CPC .............. *G06F 3/013* (2013.01); *A61B 3/113* (2013.01); *G02B 27/0093* (2013.01);
(Continued)

(58) Field of Classification Search
CPC . G06F 3/013; G02B 27/0093; G02B 27/0103; G02B 27/0172; G02B 2027/0105; A61B 3/113
(Continued)

(56) References Cited

U.S. PATENT DOCUMENTS 3,724,932 A * 4/1973 Cornsweet ............... A61B 3/10
351/210
3,804,496 A * 4/1974 Crane .................... A61B 3/113
351/210
(Continued)

FOREIGN PATENT DOCUMENTS

EP        2841991 A1    3/2015
WO   2009126264 A2   10/2009
(Continued)

OTHER PUBLICATIONS

Gramatikov et al., "Directional eye fixation sensor using birefringence-based foveal detection," Applied Optics, vol. 46, No. 10, Apr. 1, 2007, pp. 1809-1818.
(Continued)

*Primary Examiner* — William R Alexander
*Assistant Examiner* — Ephrem Z Mebrahtu
(74) *Attorney, Agent, or Firm* — Leydig, Voit & Mayer, Ltd.

(57) ABSTRACT

A method, computer readable medium, and system are disclosed for gaze tracking. The method includes the steps of receiving reflected light rays at an optical sensor, where all of the reflected light rays converge towards a rotational center of an eye and generating pattern data based on intersections of the reflected light rays at a surface of the optical sensor. A processor computes an estimated gaze direction of the eye based on the pattern data.

15 Claims, 12 Drawing Sheets

(51) Int. Cl.
 *G06K 9/00* (2006.01)
 *G02B 27/00* (2006.01)
 *G02B 27/01* (2006.01)
(52) U.S. Cl.
 CPC ..... *G02B 27/0103* (2013.01); *G02B 27/0172* (2013.01); *G06F 3/01* (2013.01); *G06K 9/00604* (2013.01); *G02B 2027/0105* (2013.01); *G02B 2027/0174* (2013.01); *G02B 2027/0187* (2013.01)
(58) Field of Classification Search
 USPC ........... 351/209, 210; 348/78, 169; 382/103, 382/117
 See application file for complete search history.

(56) References Cited

U.S. PATENT DOCUMENTS

| | | | |
|---|---|---|---|
| 4,099,841 A | 7/1978 | Ellis | |
| 4,688,879 A | 8/1987 | Fairchild | |
| 5,071,209 A | 12/1991 | Chang et al. | |
| 5,315,417 A | 5/1994 | Moss et al. | |
| 5,325,133 A | 6/1994 | Adachi | |
| 5,410,376 A * | 4/1995 | Cornsweet | A61B 3/113 351/209 |
| 5,610,673 A | 3/1997 | Rafal et al. | |
| 5,684,561 A | 11/1997 | Yancey | |
| 5,808,589 A | 9/1998 | Fergason | |
| 5,861,940 A | 1/1999 | Robinson et al. | |
| 6,027,216 A | 2/2000 | Guyton et al. | |
| 6,351,335 B1 | 2/2002 | Perlin | |
| 6,637,883 B1 | 10/2003 | Tengshe et al. | |
| 6,781,606 B2 | 8/2004 | Jouppi | |
| 6,932,475 B2 | 8/2005 | Molebny et al. | |
| 7,488,072 B2 | 2/2009 | Perlin et al. | |
| 7,747,068 B1 | 6/2010 | Smyth et al. | |
| 7,967,444 B2 | 6/2011 | Hung et al. | |
| 8,094,169 B2 | 1/2012 | Shimizu | |
| 8,529,063 B2 | 9/2013 | Bonnin et al. | |
| 9,040,923 B2 | 5/2015 | Sprague et al. | |
| 9,071,742 B2 | 6/2015 | Birkbeck et al. | |
| 9,582,075 B2 | 2/2017 | Luebke | |
| 9,737,209 B2 | 8/2017 | Gramatikov et al. | |
| 2002/0049389 A1 * | 4/2002 | Abreu | A61B 3/1241 600/558 |
| 2010/0149073 A1 * | 6/2010 | Chaum | G02B 27/0093 345/8 |
| 2012/0307208 A1 | 12/2012 | Trousdale | |
| 2014/0152558 A1 | 6/2014 | Salter et al. | |
| 2015/0200220 A1 * | 7/2015 | Juenger | H01L 27/14621 257/432 |
| 2016/0033771 A1 | 2/2016 | Tremblay et al. | |
| 2016/0202757 A1 * | 7/2016 | Miao | H04N 5/33 348/78 |
| 2016/0309081 A1 | 10/2016 | Frahm et al. | |
| 2016/0349516 A1 | 12/2016 | Alexander et al. | |
| 2016/0379606 A1 | 12/2016 | Kollin et al. | |
| 2017/0007123 A1 | 1/2017 | Samec et al. | |
| 2017/0014026 A1 | 1/2017 | Guyton et al. | |
| 2017/0075421 A1 | 3/2017 | Na et al. | |
| 2017/0115483 A1 | 4/2017 | Aleem et al. | |
| 2017/0196451 A1 | 7/2017 | Tian | |
| 2017/0205876 A1 | 7/2017 | Vidal et al. | |
| 2017/0285343 A1 * | 10/2017 | Belenkii | G02B 27/0172 |
| 2018/0164592 A1 | 6/2018 | Lopes et al. | |
| 2018/0246336 A1 * | 8/2018 | Greenberg | G02B 27/0172 |

FOREIGN PATENT DOCUMENTS

| | | |
|---|---|---|
| WO | 2016105284 A1 | 6/2016 |
| WO | 2016113533 A2 | 7/2016 |
| WO | 2016160099 A2 | 10/2016 |
| WO | 2017096241 A1 | 6/2017 |
| WO | 2017145154 A1 | 8/2017 |

OTHER PUBLICATIONS

Wang et al., "Pupil and Glint Detection Using Wearable Camera Sensor and Near-Infrared LED Array," Sensors, vol. 15, No. 12, Dec. 2015, pp. 30126-30141.

Mollers, M., "Calibration-Free Gaze Tracking an Experimental Analysis," Diploma Thesis for Computer Science Department at RWTH Aachen University, Nov. 6, 2007, pp. 1-111.

Tobii Tech, "What is Eye Tracking?" 2017, pp. 1-2, as retrieved from https://www.tobii.com/tech/technology/what-is-eye-tracking/.

Aksit et al., "Dynamic exit pupil trackers for autostereoscopic displays," Optics express, vol. 21, No. 12, 2013, pp. 14331-14341.

Ando et al., "Head Mounted Display for Mixed Reality using Holographic Optical Elements," Memoirs—Faculty of Engineering, Osaka City University, vol. 40, 1999, pp. 1-6.

Mukawa et al., "A Full Color Eyewear Display using Holographic Planar Waveguides," SID 08 Digest, Society for Information Display, 2008, pp. 89-92.

Lopes et al., U.S. Appl. No. 15/815,485, filed Nov. 16, 2017.

Guttag, K., "Mira Prism and Dreamworld AR—(What Disney Should Have Done?)," Karl Guttag on Technology, 2017, pp. 1-34 retrieved from http://www.kguttag.com/tag/mr/ on Sep. 28, 2017.

Guttag, K., "AR/MR Combiners Part 2—Hololens," Karl Guttag on Technology, Oct. 27, 2016, pp. 1-6.

Altexsoft, "Augmented Reality Check: Get Ready to Ditch Your Smartphone for Goggles," May 26, 2017, pp. 1-18, retrieved from https://www.altexsoft.com/blog/engineering/augmented-reality-check-get-ready-to-ditch-your-smartphone-for-goggles/.

Embitel, "How Combiner Glass in Head-Up Display (HUD) works?," Embitel, May 31, 2017, pp. retrieved from https://www.embitel.com/blog/embedded-blog/how-combiner-glass-in-head-up-display-hud-works.

Hong et al., "See-through optical combiner for augmented reality head-mounted display: index-matched anisotropic crystal lens," Scientific Reports, vol. 7, Jun. 5, 2017, pp. 1-11.

Li et al., "Review and analysis of avionic helmet-mounted displays," Optical Engineering, vol. 52, No. 11, Nov. 2013, 15 pages.

Amitai et al., "Visor-display design based on planar holographic optics," Applied Optics, vol. 34, No. 08, Mar. 10, 1995, pp. 1352-1356.

Guillaumee et al., "Curved Holographic Combiner for Color Head Worn Display," Journal of Display Technology, vol. 10, No. 6, Jun. 2014, pp. 444-449.

Bellini et al., "Virtual & Augmented Reality: Understanding the race for the next computing platform," Equity Research, Jan. 13, 2016, pp. 1-30.

Bekerman et al., "Variations in Eyeball Diameters of the Healthy Adults," Journal of Ophthalmology, vol. 2014, Article ID 503645, 2014, pp. 1-5.

Curran, C., "The road ahead for augmented reality," Apr. 1, 2016, pp. 1-14, retrieved from http://www.pwc.com/us/en/technologyforecast/augmented-reality/augmented-reality-road-ahead.htm.

Merel, T., "Augmented and Virtual Reality to Hit $150 Billion, Disrupting Mobile by 2020," Crunch Network, Apr. 6, 2015, pp. 1-9, retrieved from https://techcrunch.com/2015/04/06/augmented-and-virtual-reality-to-hit-150-billion-by-2020/.

Kim et al., "Analysis of a head-mounted display-type multifocus display system using a laser scanning method," Optical Engineering, vol. 50, Issue 3, Mar. 2011.

Jian-Nan et al., "Key Techniques of Eye Gaze Tracking Based on Pupil Corneal Reflection," Global Congress on Intelligent Systems, IEEE Computer Society, 2009, pp. 133-138.

Sigut et al. "Iris Center Corneal Reflection Method for Gaze Tracking Using Visible Light," IEEE Transactions on Biomedical Engineering, vol. 58, No. 2, Feb. 2011, pp. 411-419.

Lee et al., "Effects of Optical Combiner and IPD Change for Convergence on Near-Field Depth Perception in an Optical See-Through HMD," IEEE Transactions on Visualization and Computer Graphics, vol. 22, No. 5, May 2016, pp. 1540-1554.

(56) References Cited

OTHER PUBLICATIONS

Li et al., "Holographic display for see-through augmented reality using mirror-lens holographic optical element," Optics Letters, vol. 41, No. 11, Jun. 1, 2016, pp. 2486-2489.

* cited by examiner

SYSTEMS AND METHODS FOR GAZE TRACKING

CLAIM OF PRIORITY

This application claims the benefit of U.S. Provisional Application No. 62/432,454 titled "Gaze Tracking and Optical Combiner," filed Dec. 9, 2016, the entire contents of which is incorporated herein by reference.

FIELD OF THE INVENTION

The present invention relates to gaze tracking, and more particularly to gaze tracking where all reflected light rays converge towards a rotational center of an eye.

BACKGROUND

Augmented reality (AR) and virtual reality (VR) devices have the potential ability to replace desktop monitors and mobile computing platforms (such as smart phones). Mobile AR and VR devices; however, currently face many challenges. Extremely large data transfer rates will be needed to transfer images to head mounted displays with the same resolution as today's 2 k or 4 k displays used in televisions or high end smart phones. Battery life on devices which are not wired directly to a computer are limited due to the power requirements of conventional technologies. These issues illustrate the need for a low power, fast gaze tracker which could be integrated into Augmented Reality (AR) or Virtual Reality (VR) Head Mounted Displays (HMDs). Thus, there is a need for addressing these issues and/or other issues associated with the prior art.

SUMMARY

A method, computer readable medium, and system are disclosed for gaze tracking. The method includes the steps of receiving reflected light rays at an optical sensor, where all of the reflected light rays converge towards a rotational center of an eye and generating pattern data based on intersections of the reflected light rays at a surface of the optical sensor. A processor computes an estimated gaze direction of the eye based on the pattern data.

DETAILED DESCRIPTION

A fast gaze tracker, integrated with a foveated rendering or foveated display scheme, simultaneously reduces the needed data transfer rate to head-mounted displays as well as reduces the computational cost of displaying high quality images. Having fast, low power gaze tracking technology opens up the possibility of a gaze-based input interface, gaze-contingent content generation, biometrics, and many other opportunities. In head-mounted displays, gaze tracking may provide low latency and a high sampling rate. Gaze tracking measures the orientation of the viewer's eyes and, therefore, must consider the structure of the eye and account for alignment of the gaze tracker with respect to the viewer. For example, the alignment may change when a position of a head-mounted display shifts relative to the viewer's eyes.

Figure 1A:
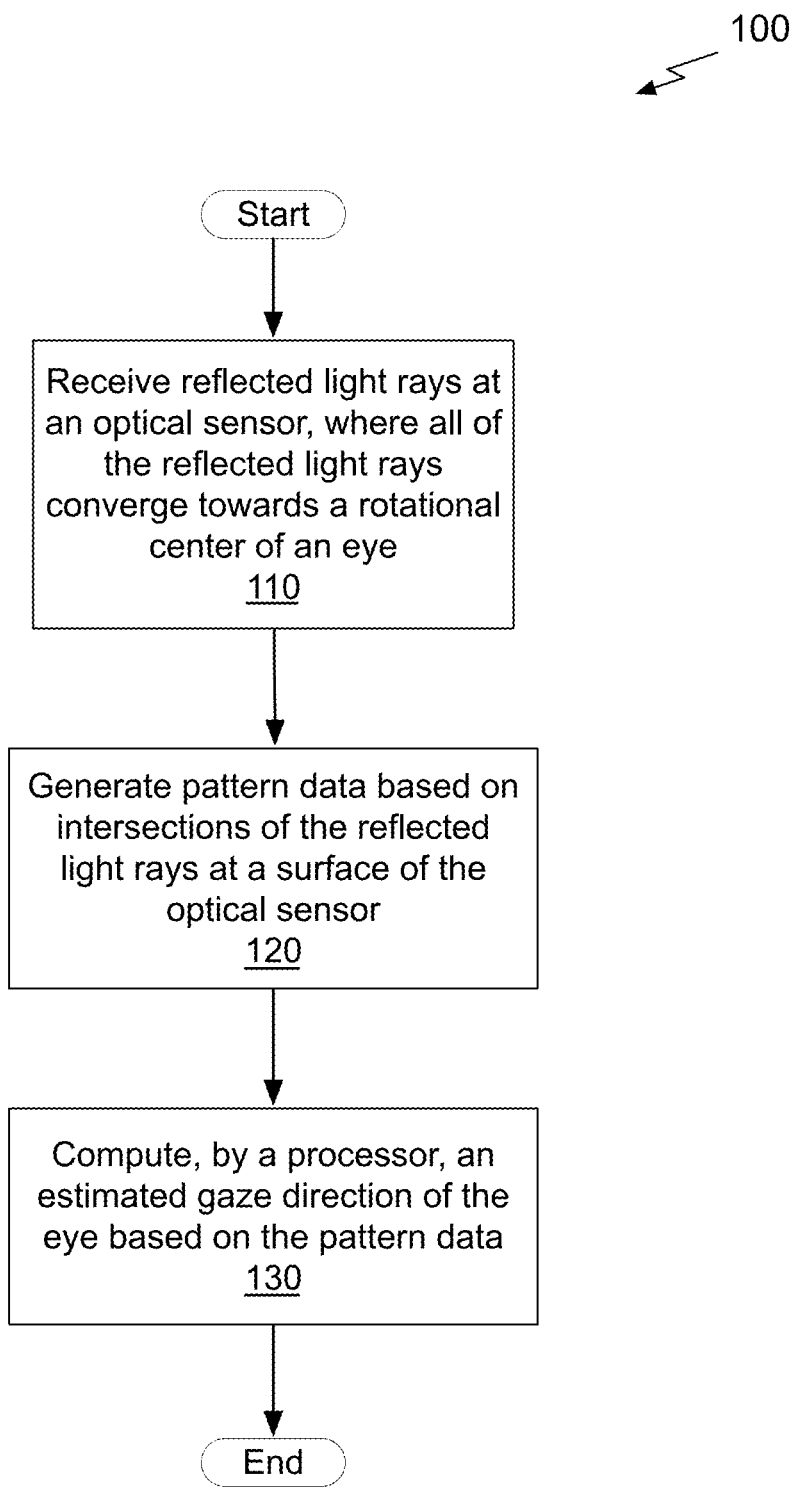
FIG. 1A illustrates a flowchart of a method for gaze tracking, in accordance with one embodiment.

FIG. 1A illustrates a flowchart 100 of a method for gaze tracking, in accordance with one embodiment. Although method 100 is described in the context of a processing unit, the method 100 may also be performed by a program, custom circuitry, or by a combination of custom circuitry and a program. For example, the method 100 may be executed by a GPU (graphics processing unit), CPU (central processing unit), neural network, or any processor capable of computing the gaze direction based on patterns detected by an optical sensor. Furthermore, persons of ordinary skill in the art will understand that any system that performs method 100 is within the scope and spirit of embodiments of the present invention.

A gaze tracking technique illuminates a viewer's eye with light rays that converge towards the rotational center of the eye. When the light rays converge pass through or intersect the rotational center of the eye, the geometrical relationship between the light rays and the eye surface are consistent regardless of the gaze direction of the eye (i.e., direction in three-dimensional space projected outward from the eye from the rotational center of the eye through the center of the pupil). Changes in the gaze direction may be specified by two angles, such as a first angle in the horizontal direction and a second angle in the vertical direction. In one embodiment, the light rays that converge towards the rotational center of the eye are then reflected by the retina, crystalline lens, or cornea, producing reflected light rays. At step 110, the reflected light rays are received at an optical sensor, where all of the reflected light rays converge towards the rotational center of an eye. The reflected light rays converge to intersect at the rotational center of the eye under a special condition when the light rays are retro-reflected (meaning the incident path and the reflected path are the same) off the retina. However, only a small portion of all the reflected light rays is typically retro-reflected. Instead, most of the reflected light rays deviate slightly from a path that converges to intersect at the rotational center of the eye. In the context of the following description, the reflected light rays converge towards the rotational center of the eye, meaning that the reflected light rays may intersect the rotational center of the eye or pass near the rotational center of the eye, such as within 1 mm of the rotational center of the eye. In one embodiment, the rotational center of the eye is defined to include a single point at the precise rotational center of the eye and points within 1 mm of the single point in any direction. In one embodiment, the rotational center of the eye is defined to include a single point at the precise rotational center of the eye and points within 2 mm of the single point in any direction. In one embodiment, the reflected light rays converge towards a conjugate point of the rotational center of the eye, where the conjugate point is an optical "copy" of the rotational center of the eye. When the light rays are reflected off the cornea or crystalline lens, all of the reflected light rays, when extended into the eye, converge to intersect at the rotational center of the eye.

In one embodiment, the optical sensor is a camera. In another embodiment, the optical sensor is a quadrant photo detector. A light pattern is produced at the optical sensor by the light rays reflected from the eye. In one embodiment, a simple low-power image sensor is used to detect the light pattern and complicated signal processing is avoided. At step 120, pattern data is generated based on intersections of the reflected light rays at a surface of the optical sensor. In one embodiment, the optical sensor is positioned at an origin of the light rays.

At step 130, a processor computes an estimated gaze direction of the eye based on the pattern data. The gaze direction may then be mapped to a position on a display screen corresponding to a viewer's gaze. Patterns of light rays that are received at the surface of the optical sensor may be used to determine changes in the gaze direction for gaze tracking. In one embodiment, the light sensor generates signals according to the patterns and the signals are converted into pattern data, such as displacement values. In one embodiment, the mapping between the displacement of the reflected light rays indicated by the pattern data and the gaze change is a linear function. In another embodiment, the mapping the displacement of the reflection indicated by the pattern data and the gaze change is a quadratic function. As a result of the simple calculation used to map the displacements to direction changes, the latency for gaze tracking is reduced and the sampling rate may be increased.

More illustrative information will now be set forth regarding various optional architectures and features with which the foregoing framework may or may not be implemented, per the desires of the viewer. It should be strongly noted that the following information is set forth for illustrative purposes and should not be construed as limiting in any manner. Any of the following features may be optionally incorporated with or without the exclusion of other features described.

Human eyes can rotate very quickly. Saccades reaching 200 deg/sec of rotation happen commonly, two or three times every second. In the extreme, saccades can easily rotate as fast as 1000 deg/sec during vestibulo-ocular reflex (the counter-rotation of the eyes for maintaining focus on a fixed object while the head is turning). AR and VR devices must react to such fast eye movements immediately for at least two reasons. First, latency is known to be a critical factor for maintaining viewer's immersive experiences. Second, the computational savings of foveated rendering is closely dependent on how quickly the system responds to the actions of the viewer, i.e. how short the latency is. A common consensus in industry is that latency must be kept below 20 ms. Gaze trackers, being the first step of a hardware pipeline for gaze-interactive systems, should achieve as low a latency as possible. Most conventional consumer-level gaze trackers introduce ~10 ms of latency, leaving only 10 ms for the rest of the pipeline (rendering, data transmission, and image presentation). Reducing the latency due to gaze tracking is needed to improve the viewer's experience. Sampling rates constrain latency because the gaze tracker cannot return results faster than the viewing position of the viewer is obtained. In this sense, high sampling rates and low latencies are related. On the other hand, high sampling rates allow fast eye movements to be followed more precisely. Gaze trackers with high sampling rates can capture the dynamics of eye movements more accurately, providing a way to associate biometrics with eye movements.

Power consumption is typically an issue for mobile AR and VR devices. Most conventional video-based gaze trackers consume a considerable amount of power for capturing and processing images of the eyes. Power consumption can be reduced by either reducing the complexity of the calculations required to interpret the images provided by the gaze tracking camera or by performing gaze tracking using a detector that consumes less power than a camera. Simplification of the signal encoding the pattern data that are provided by a detector simplifies the computations needed to interpret the signal to generate an estimated gaze direction, thereby reducing latency and power consumption. The signal encoding the pattern data may be simplified by exploiting the geometrical structure of the eye. In one embodiment, the signal corresponds to one or more illumination intensity values.

Figure 1B:
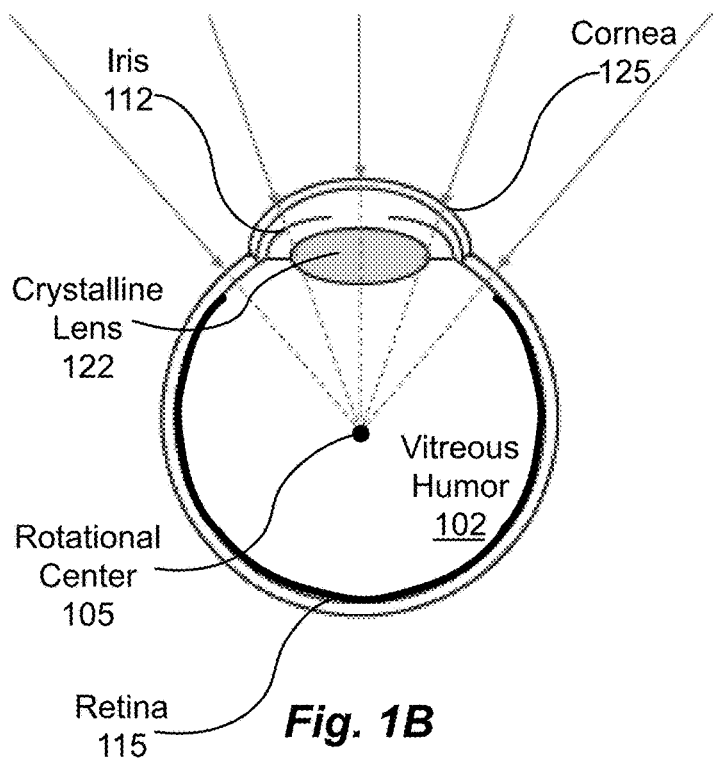
FIG. 1B illustrates a rotational center of the eye, in accordance with one embodiment.

FIG. 1B illustrates a rotational center of the eye, in accordance with one embodiment. Overall, the eye is generally spherical. The exception to this shape is the frontal part of the eye that contains the lens structures that focus the image of the outside world onto the back on the eyeball. Specifically, the frontal part of the eye includes a crystalline lens 122, iris 112, and cornea 125. The region between the cornea 125 and crystalline lens 122 is filled with aqueous humor.

Light rays (shown as arrows converging towards the rotational center 105 of the eye) entering the eye through a pupil (an opening in the iris 112) pass through multiple layers having different shapes and refractive indices. The cornea 125 is the medium that the incident light first encounters, causing the greatest refraction of the light rays due to a high refractive index (~1.376) and small radii of curvature (7.84 mm for the anterior surface and 6.4 mm for the posterior surface).

The light rays then travel through the aqueous humor, whose refractive index is close to that of water (1.34). After that, the light rays pass through the iris 112 that adjusts the size of the pupil depending on the brightness of the visual scene. Light not occluded by the iris proceeds to meet the crystalline lens 122, having a refractive index (1.44) that is higher than the aqueous humor and a variable radius of curvature. The crystalline lens 122 allows the eye to focus at different distances. Behind the crystalline lens 122 is another liquid, the vitreous humor 102 (refractive index=1.34), which fills most of the eyeball. Finally, the light rays arrive at the retina 115 after passing through the vitreous humor 102. At the retina 115 some portion of the light is absorbed by the photoreceptors, initiating processing of the visual signal. The unabsorbed portion is diffusively reflected by the retina 115, and some portion of the light passes through the pupil and escapes the eye.

When light travels across two optical media with different refractive indices, some portion of the light reflects off the interface between the two media (Fresnel reflection) and the remaining portion is refracted, changing the direction of the light. The amounts of the light that are reflected and refracted are determined by Fresnel's equations and the angle of refraction is determined by Snell's law. As shown in FIG. 1B, there are four places in the frontal structure of the eye where Fresnel reflections can happen (e.g., Purkinje reflections): front and back surfaces of the cornea 125 and front and back surfaces of the crystalline lens 122. Light reflected off of the retina 115 propagates along the path that the light travels to enter the eye—traveling backwards towards the original source of the light rays. The portion of the light that is reflected off of the retina 115 causes the (distressing) red-eye effect which is observable in photos taken with a flash at night.

As shown in FIG. 1B, the light rays converging towards the rotational center 105 of the eye form a cone shape. Typically, only a portion of the light rays are reflected back by one or more of the front surface of the cornea 125, back surface of the cornea 125, the front surface of the crystalline lens, the back surface of the crystalline lens, and the retina 115. The portion of the reflected light rays form a smaller cone shape compared with the cone shape formed by the converging light rays. A pattern may be observed when the reflected light rays intersect a surface.

Despite the presence of complicated optical interactions for various structures of the eye, the pattern of light reflected from the eye is not that complicated. Because the optical components in the eye are all specialized at forming focused images, the reflected patterns are also simple. Moreover, the optical structure of the eye is aligned about the optical axis of the eye that originates at the retina 115 and passes through the rotational center 105 and pupil and exiting the eye through the center of the cornea 125. The optical axis of the eye corresponds to the gaze direction (i.e., visual axis), although the optical axis and the gaze direction may not be coincident. More specifically, for each individual there is a constant deviation between the optical axis and the gaze direction that is usually less than or equal to 5°. Using on-axis illumination, which itself is also rotationally symmetric about the optical axis of the eye regardless of the gaze direction, the structure of the reflected light will remain simple and easy to interpret. The geometrical relationship between the surfaces of the optical components and the illumination should remain constant for any gaze direction. As a result of the constant geometrical relationship, the reflection pattern—no matter what shape it is—will also be constant and will shift in space together with the gaze direction. Consequently, complicated image processing, which is often burdensome for video-based gaze trackers, is avoided.

Referring to FIG. 1B, the light rays are directed towards the rotational center 105 of the eye and the gaze direction coincides with the light ray entering through the center of the pupil that is also aligned with the optical axis of the eye. All other light rays and structure of the eye are rotationally symmetric around the gaze direction. Note that the geometrical relationship remains the same if the gaze direction of the eye changes (e.g. the light ray that enters through the center of the new pupil location will again coincide with the new gaze direction). Independent of gaze direction, the relationship between the eye's geometry and the direction of the impinging light rays that converge towards the rotational center 105 remains the same. The pattern of the reflected light, therefore, only shifts in space.

Figure 1C:
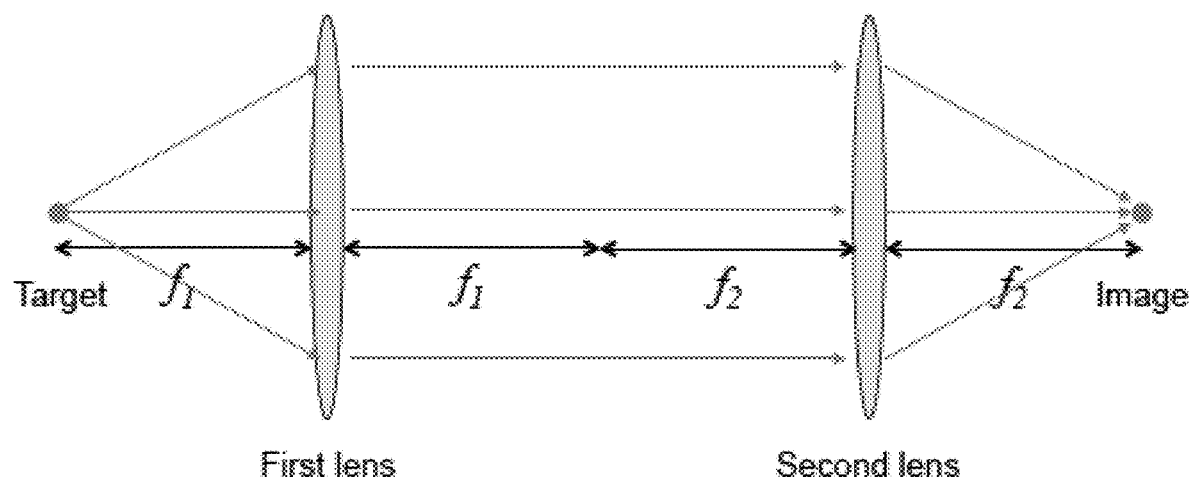
FIG. 1C illustrates a prior art 4f system for creating a converging light source.

FIG. 1C illustrates a prior art 4f system for creating a converging light source. One mechanism for creating a converging set of rays is to start with a diverging set of rays and then turn the set into a converging set using optical components. Converging rays are generated using a conventional optical configuration known as a 4f system. A 4f system is composed of two convex lenses. The name 4f originates from the spacing between the target, the two lenses, and the image. The first lens is separated from the target by the focal length of the first lens ($f_1$); the second lens is separated from the first lens by the sum of the two lenses' focal lengths; and, the image is separated from the second lens by the focal length of the second lens ($f_2$). In 4f systems, the target and image planes have a special relationship with each other: the set of rays which appear in the target plane are reproduced in the image plane with the same geometrical relationships (with the caveat that the set of rays are inverted about the optical axis). Because of this relationship, the two planes are referred to as conjugate planes.

Figure 1D:
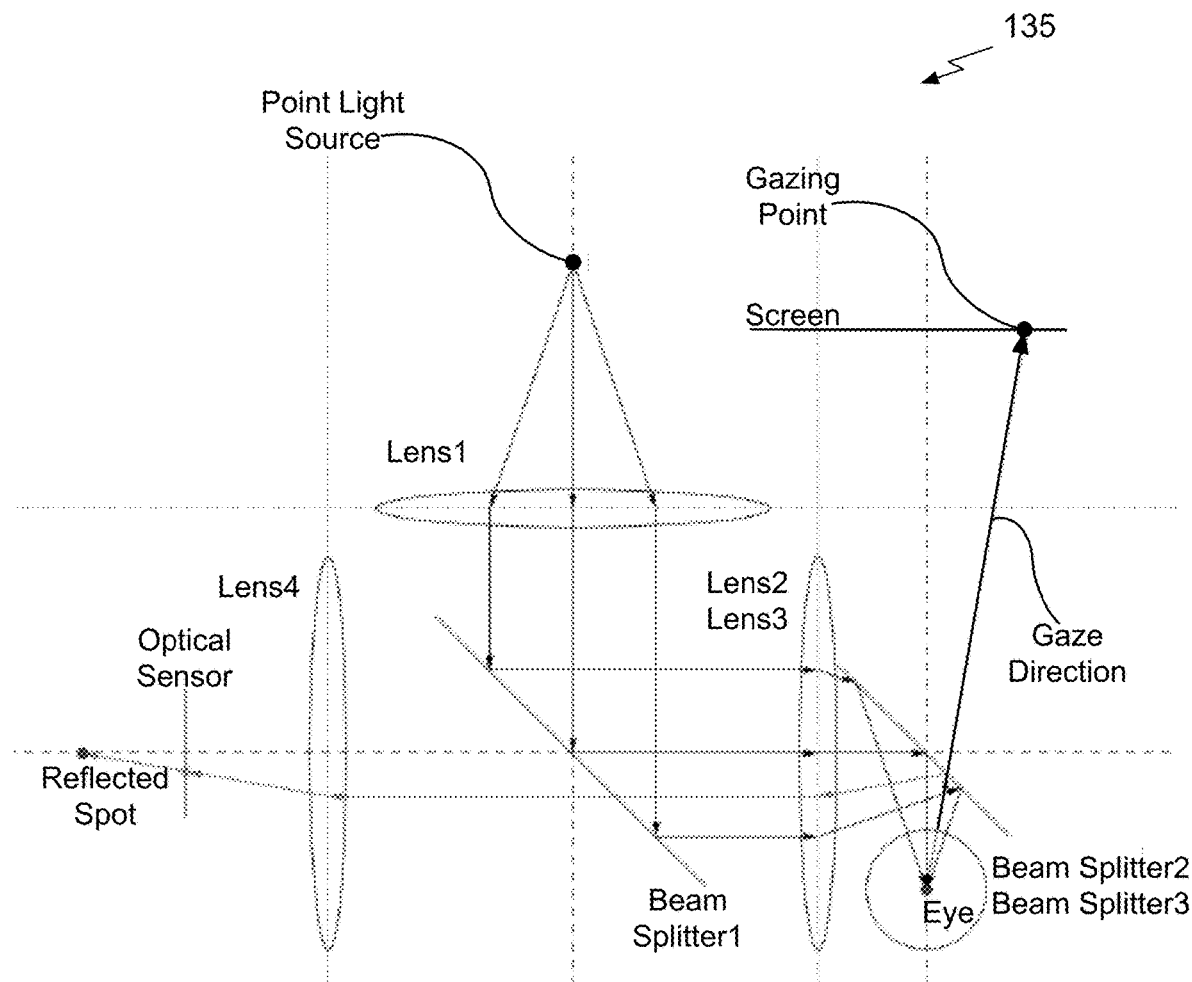
FIG. 1D illustrates an 8f system for creating converging rays for the eye, in accordance with one embodiment.

FIG. 1D illustrates an 8f system 135 for creating converging rays for the eye, in accordance with one embodiment. As shown in FIG. 1D, the 8f system 135 includes three convex lenses, where one of the three lenses is used twice (as lens2 and lens3). The 8f system 135 also includes two beam splitters, where the beam splitter 2 is used twice (as Beam splitter2 and Beam splitter3). An on-axis illumination is generated by Lens1, a Beam splitter1, Lens2, and a Beam splitter2. The Lens1, Beam splitter1, Lens2, and Beam splitter2 create light rays that converge towards the rotational center of the eye. Then the converging light rays are reflected by the eye and transferred to an optical sensor via the Beam splitter3, Lens3, and Lens4. The beam splitter3, the lens3, and the len4 are optical elements configured to direct the reflected light rays along a path to reach the optical sensor. The transferred light rays form reflection patterns at the surface of the optical sensor. The 8f system 135 may be implemented using over-the-counter optical components. However, the 8f system 135 is bulky and not suitable to be integrated into head-mounted AR/VR devices.

At a high level, the objective of the 8f system 135 is to create an on-axis illumination system for the eye and then to detect displacement of the reflected light to estimate the gaze direction. In terms of implementation, a gaze tracking hardware system breaks includes three components: relay optics, a light source, and a detector. There are several possible hardware choices for each of the three components. While example implementations are provided, possible implementations of systems that detect displacements of reflected light to estimate gaze direction are not limited to those described.

Figure 1E:
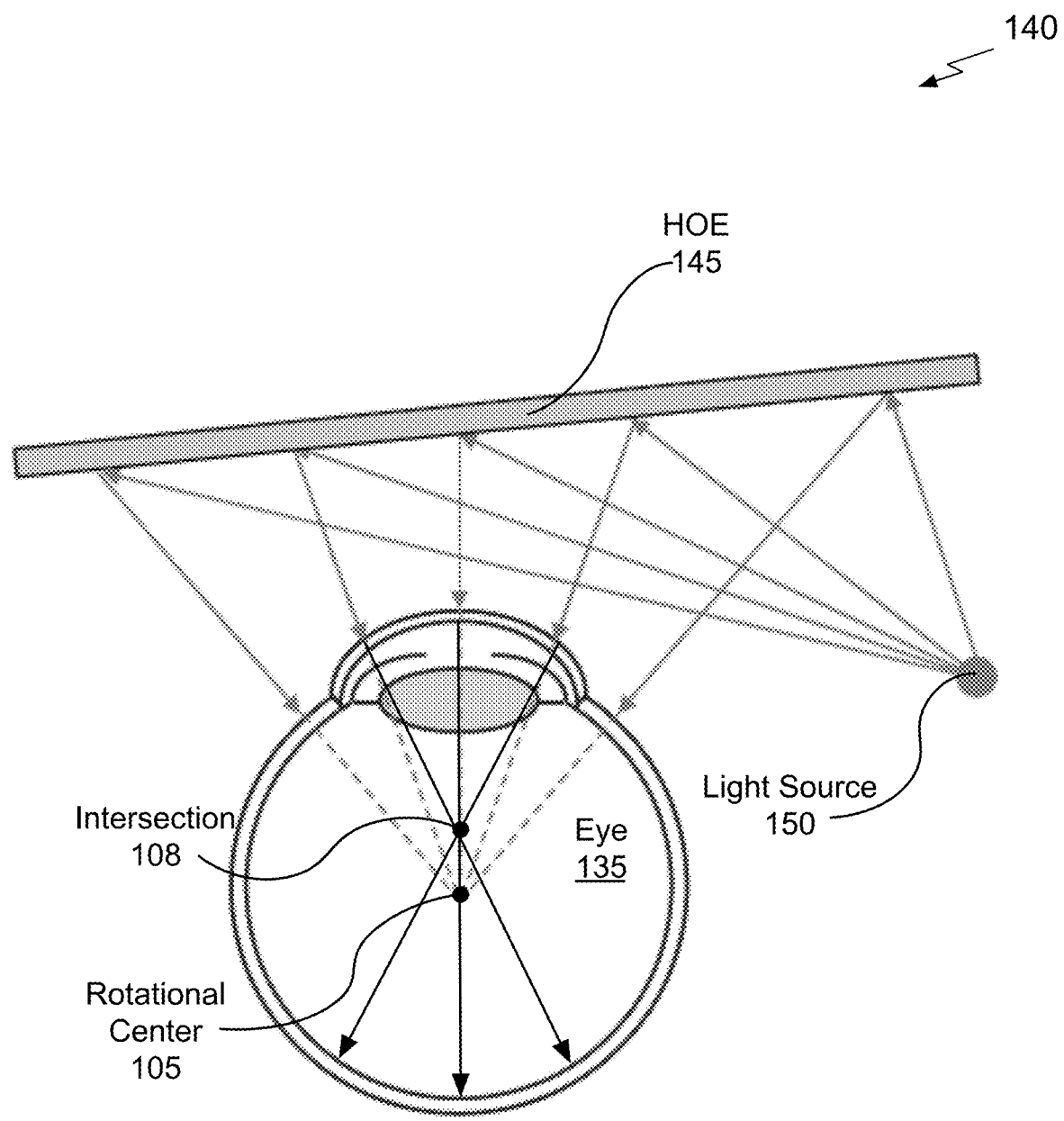
FIG. 1E illustrates a holographic optical element (HOE) system for creating converging rays for the eye, in accordance with one embodiment.

FIG. 1E illustrates a holographic optical element (HOE) system 140 for creating converging rays for an eye 135, in accordance with one embodiment. Compared with the 8f system 135, the volume of the transfer optics is reduced when an HOE 145 is used to generate the converging light rays. The HOE 145 changes the direction of light rays which impinge on the holographic element. An appropriately configured HOE 145 will receive a set of diverging rays (the reference beam) and convert the set of diverging rays into a set of converging rays (the object beam). As shown in FIG. 1E, a set of diverging light rays is generated by a light source 150 and converted, by the HOE 145, into the set of light rays that converge towards the rotational center 105 of the eye 135.

For light rays traveling in a direction opposite to that of the object beam (i.e., light rays reflected by the eye), the path of travel is reversed, and, upon interaction with the HOE 145, the light rays travel in the opposite direction of the reference beam. When the reflected light rays reflect off the cornea of the eye 135 and, when each reflected light ray is extended into the eye 135, all of the reflected light rays converge to originate at the rotational center 105 of the eye 135.

The HOE 145, therefore, serves a similar function to that of the Lens1, Beam splitter1, Lens2, and Beam splitter2 in the 8f system 135. An advantage of HOEs, including the HOE 145, is that it becomes nearly transparent to light rays that are different in terms of wavelength or propagation direction compared with the reference beam and object beam. Therefore, an HOE 145 may be used to create the desired illumination in AR and VR devices without occluding a view of the environment. The overall configuration of the HOE system 140 is also well-suited for light-weight and compact AR and VR devices because only a single HOE 145 is needed.

Figure 2A:
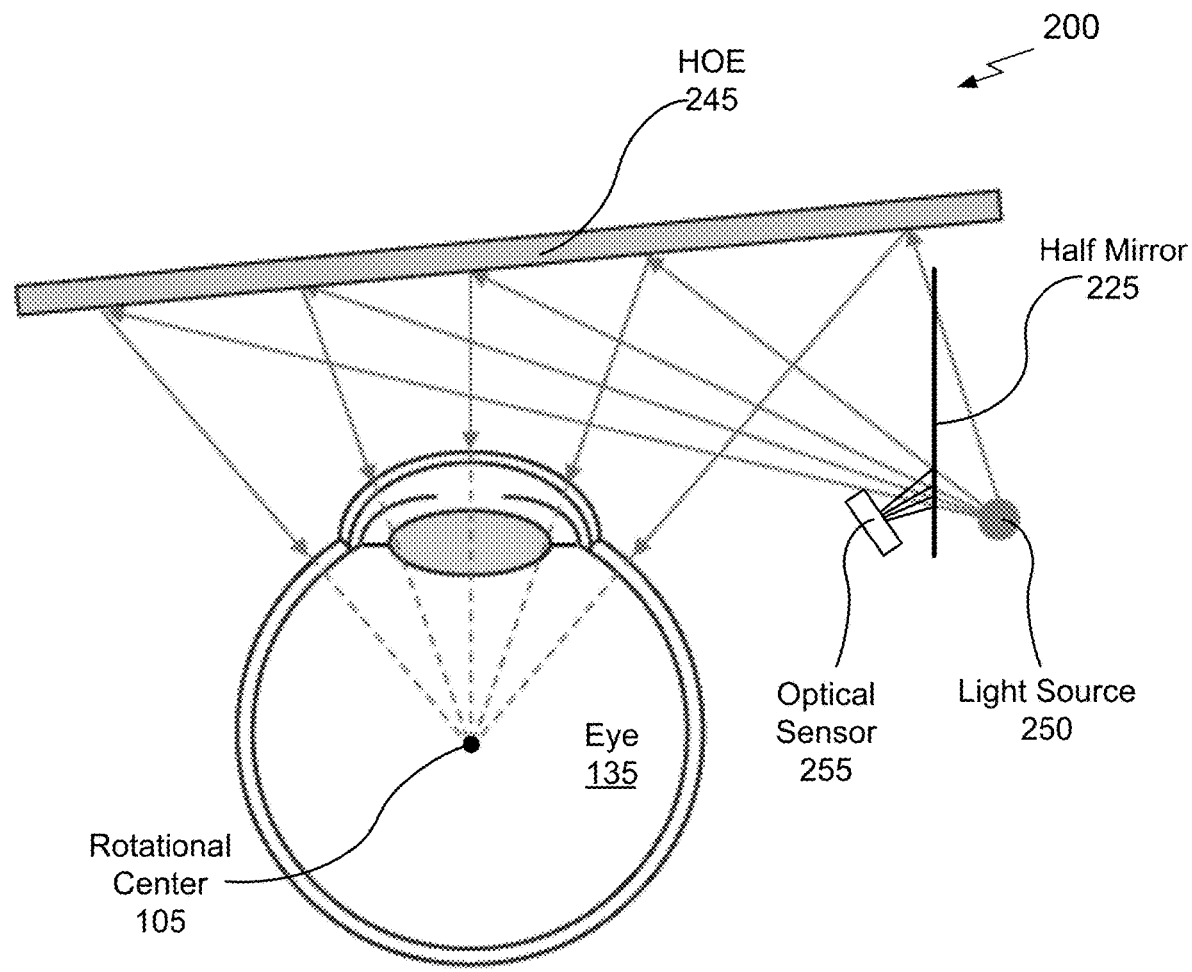
FIG. 2A illustrates an HOE system including an optical sensor, in accordance with one embodiment.

FIG. 2A illustrates an HOE system 200 including an optical sensor, in accordance with one embodiment. Like the HOE system 140, the HOE system 200 includes an HOE 245 and a light source 250. The HOE system 200 also includes a half mirror 225 and an optical sensor 255. The half mirror 225 transmits light rays from the light source 250 and reflects light rays that are reflected by the eye and redirected by the HOE 245 toward the optical sensor 255. A first path of the light rays originating at the light source 250 is redirected by the HOE 245 to converge at a rotational center 105 of the eye 135. The light rays terminate at either the cornea or the retina where the light rays are reflected. Light rays that terminate at the cornea converge towards the rotational center 105, and, if extended into the eye would pass through the rotational center 105. Light rays that terminate at the retina pass through the rotational center 105.

The reflected light rays traverse a second path that is coincident or nearly coincident with the first path until the reflected light rays intersect the half mirror 225. In one embodiment, the nearly coincident second path is within 1 mm of the first path. The reflected light rays are then reflected by the half mirror 225 towards the optical sensor 255. The HOE 245 and the half mirror 225 are optical elements configured to direct the reflected light rays along a path to reach the optical sensor 255. The optical sensor 255 is described in conjunction with FIG. 2B.

In one embodiment, the light source 150 generates infrared light. Infrared light is often the choice of illumination for gaze tracking because it is invisible to the viewer. Unlike ultraviolet (UV) light, infrared illumination is harmless to the eye when the intensity of the infrared light is below the safety threshold for the photoreceptors. An infrared light-emitting diode (LED) is a simple light source for providing on-axis illumination because a bare (without other optics) LED naturally forms a source of diverging rays.

In one embodiment, the light source 150 is a projector that produces images and provides a light source for gaze tracking. When the light source 150 is a projector gaze tracking is operational while images are produced for display. However, the changing intensity of the projected images will change the intensity of the light rays that are reflected to the optical sensor and used for gaze tracking. In one embodiment, the projector generates an infrared channel, and the infrared channel is lit regardless of the images that are produced to provide a constant illumination source.

Figure 2B:
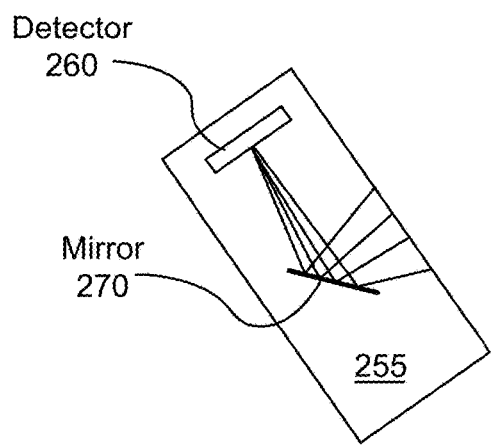
FIG. 2B illustrates the optical sensor shown in FIG. 2A, in accordance with one embodiment.

FIG. 2B illustrates the optical sensor 255 shown in FIG. 2A, in accordance with one embodiment. In one embodiment, the optical sensor 255 comprises a mirror 270 that is controlled to generate converging light rays for a detector 260. An angle of the mirror 270 may be adjusted to reflect the incoming light rays toward the detector 260 to control the position of intersections of the incoming light rays at the detector 260. The intersections of the incoming light rays produce a pattern from which pattern data is computed that specifies a change in the gaze direction. In one embodiment, the mirror 270 is adjusted to center the pattern at the detector 260. In one embodiment, the pattern data specifies a horizontal displacement and a vertical displacement.

As shown in FIGS. 1D and 2A, light reflected from the eye travels backwards through the transfer optics to a plane containing the light source, or, depending on the intervening optics, to a plane conjugate to the plane containing the light source. Changes in the gaze direction are detected as motion of the reflected light. The movement of the reflected light depends on the location of the detector. The extent of the motion becomes larger the farther the detector is from the conjugate planes. Depending on the algorithm used to analyze the motion of the reflected light, differing detectors may be used.

In one embodiment, the detector 260 is a camera sensor. Imaging optics may or may not be used depending on the choice of light source, relay optics, or strategy for signal detection. The distribution of reflected light is read as an image. Depending on where the camera sensor is positioned relative to the conjugate plane of the light source, the pattern of the reflected light rays moves in the same or opposite direction of the gaze change. Specifically, the pattern of the reflected light rays moves in the same direction when the detector plane is standing between the light source 250 and the conjugate plane of the light source 250. Compared to conventional video-based gaze tracking, the image processing can be much simpler. Instead of analyzing the shape and position of the pupil or the various Purkinje reflections, as is performed for video-based gaze tracking, simple blob detection suffices. In one embodiment, detecting a location of maximum intensity may be used to identify a change in gaze direction.

Figure 2C:
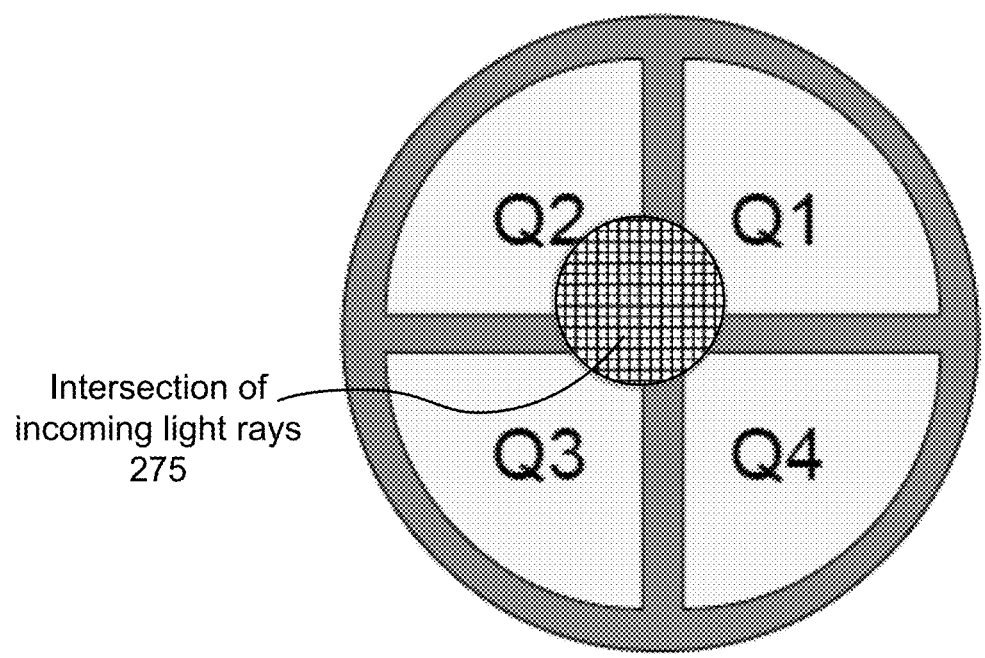
FIG. 2C illustrates a quadrant photo detector, in accordance with one embodiment.

FIG. 2C illustrates a quadrant photo detector, in accordance with one embodiment. As shown in FIG. 2C, the quadrant photo detector is a circular shape divided into four quadrants Q1, Q2, Q3, and Q4. In other embodiment, the other shapes may be used (e.g., square) and the shape may be divided into regions of equal or non-equal sizes. The quadrant photo detector may be used to implement an optical sensor capable of generating signals corresponding to a pattern that is produced when light rays are received at a surface of the quadrant photo detector. For example, a pattern formed by an intersection of incoming light rays 275 may be detected and signals encoding illumination intensity values may be used to compute pattern data corresponding to a change in the gaze direction. The quadrant photo detector may be considered to be a four-pixel "image" sensor, where each quadrant corresponds to a pixel. An illumination intensity value of each of the four pixels quantifies an intensity of the light intersecting the pixel. A horizontal and vertical displacement may be computed using the illumination intensity values.

$$\text{horizontal displacement} = \frac{[(Q2 + Q3) - (Q1 + Q4)]}{[(Q2 + Q3) + (Q1 + Q4)]}$$

-continued $$\text{vertical displacement} = \frac{[(Q1+Q2)-(Q3+Q4)]}{[(Q1+Q2)+(Q3+Q4)]}$$

Therefore, the illumination intensity values may be directly mapped to a change in the viewer's gaze position on the screen.

In one embodiment, the quadrant photo detector is located closer to the conjugate plane (when compared to with a location of a camera sensor) to capture small displacements of the reflected light rays. In one embodiment, the horizontal and vertical displacements are used to electronically control the mirror 270, steering the reflected light towards the center of the quadrant photo detector 260 and using the pixel values provided by the quadrant photo detector as feedback. A change in the viewer's gaze direction may be estimated based on the steering angle of the mirror 270.

Figure 2D:
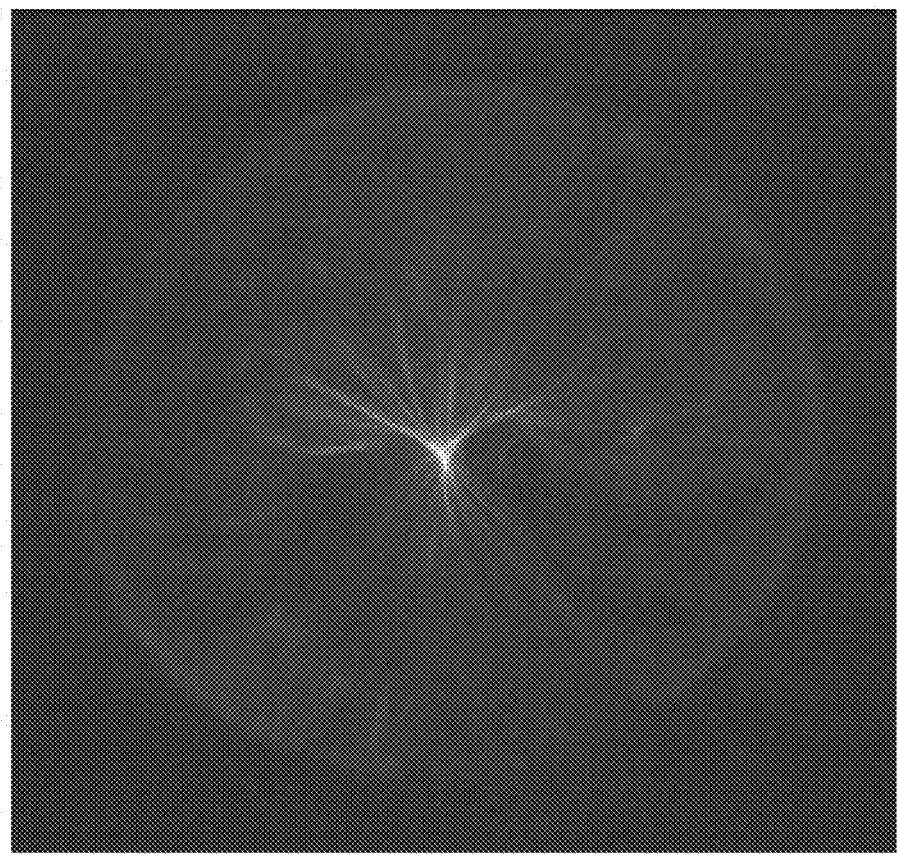
FIG. 2D illustrates a pattern reflected from the eye, in accordance with one embodiment.

FIG. 2D illustrates a pattern reflected from the eye, in accordance with one embodiment. As the direction of a viewer's gaze changes, the pattern shifts left/right and/or up/down. The reflected pattern is substantially rotationally symmetric around the optical axis of the eye. More importantly, the pattern of the reflected light does not change much as the gaze direction varies. In contrast, when conventional video-based tracking is used, the shape of pupil changes as the gaze direction varies, causing the pattern of the reflected light to change. Unlike conventional gaze tracking, the simplicity and consistency of the reflected pattern enables the use of many image processing algorithms to produce the pattern data (e.g., horizontal and vertical displacements). The reflected pattern is produced by the light rays that converge towards the rotational center 105 of the eye to produce reflected light rays that diverge away from the rotational center 105 of the eye. Even the simplest algorithm, such as searching for the pixel in the detector 260 having the maximum illumination intensity may be as effective as a more complicated technique of finding the Gaussian-weighted center of mass.

Figure 2E:
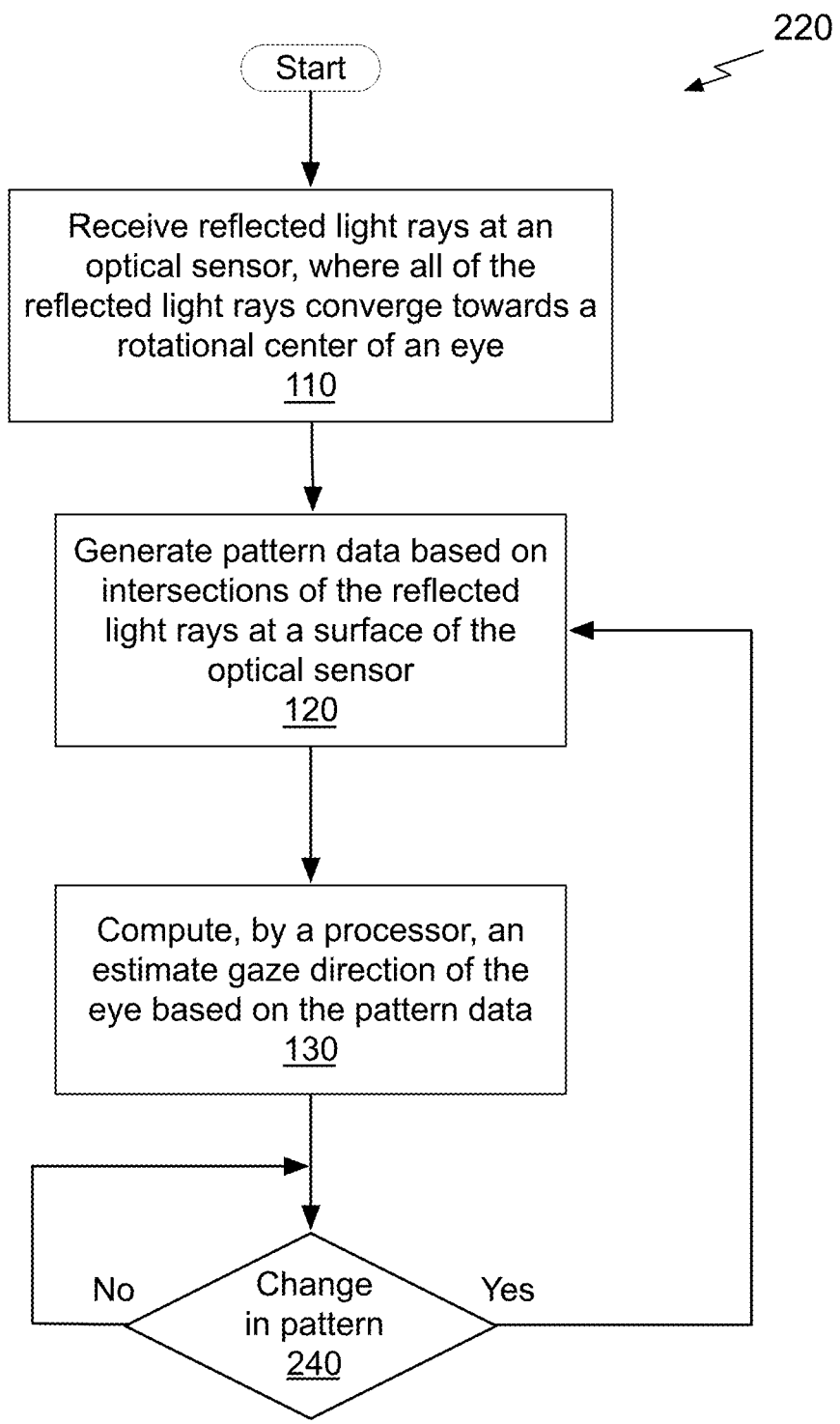
FIG. 2E illustrates a flowchart of another method for gaze tracking, in accordance with one embodiment.

FIG. 2E illustrates a flowchart of another method for gaze tracking, in accordance with one embodiment. Although method 220 is described in the context of a processing unit, the method 220 may also be performed by a program, custom circuitry, or by a combination of custom circuitry and a program. For example, the method 220 may be executed by a GPU (graphics processing unit), CPU (central processing unit), neural network, or any processor capable of computing the gaze direction based on pattern data computed based on a pattern detected by the optical sensor 255. Furthermore, persons of ordinary skill in the art will understand that any system that performs method 220 is within the scope and spirit of embodiments of the present invention.

Steps 110, 120, and 130 are performed as previously described in conjunction with FIG. 1A. Importantly, at step 110, all of the reflected light rays converge towards the rotational center 105 of the eye. A light pattern is produced at the optical sensor by the light rays reflected from the eye that intersect the optical sensor 255. At step 120, the pattern data is generated based on intersections of the reflected light rays at a surface of the optical sensor 255. In one embodiment, the optical sensor 255 is positioned away from the light source 250 (i.e., an origin of the light rays). In one embodiment, the intensity of the light pattern at one or more regions of the detector 260 is used to compute pattern data comprising a vertical and a horizontal displacement, avoiding complicated signal processing.

At step 130, a processor computes an estimated gaze direction of the eye based on the pattern data. The gaze direction may then be mapped to a position on a display screen corresponding to a viewer's gaze. In one embodiment, a steering angle of the adjustable mirror 270 is controlled to center the pattern at the surface of the optical detector 260 and a position within a display screen is computed based on the steering angle.

At step 240, the optical sensor 255 indicates if a change occurs in the pattern received at the optical sensor 255, and, if so, the gaze tracking system 200 may return to step 120 to generate updated pattern data. The updated pattern data that is computed based on signals from the optical sensor 255 may be used to determine changes in the gaze direction for gaze tracking. In one embodiment, the pattern data includes misalignment data that is also used to determine changes in the gaze direction. The misalignment data may indicate an offset, in any direction, between an original position of a head-mounted display that includes gaze tracking system 200 and a new position of the head-mounted display. In one embodiment, the offset is relative to the viewer's eye. If, at step 240, the optical sensor 255 indicates no change has occurred in the pattern received at the optical sensor 255, then the gaze tracking system 200 remains in step 240.

The relationship between the displacement of the reflected pattern at the detector 260 and changes in the gaze direction is mostly linear. In one embodiment, a linear mapping is used to convert changes in the position of the pattern into changes in the gaze direction. In another embodiment, a quadratic mapping is used to convert changes in the position of the pattern into changes in the gaze direction. In contrast, when conventional video-based gaze tracking is used, the pupil movement viewed at the camera cannot be simply transformed to compute a change in the gaze direction. In practice, relay optics may introduce some irregularity into the mapping due to aberrations in the optical elements. However, the mapping function remains simple, allowing for savings in computational power and latency.

While using a VR or AR head mounted display, rapid motion of a viewer's head is possible. For example, a viewer looking out for non-player characters may produce a gaming hazard. Rapid motion of the head is likely to subtly change the alignment of the head-mounted display device with respect to the viewer's head. As a result, the gaze tracking system 200 may become offset from the original location, introducing misalignment in the illumination. The original location and corresponding gaze direction are determined based on a calibration procedure and changes in the gaze direction and determined relative to the original gaze direction. When the alignment is offset, the assumption of on-axis illumination is no longer valid. If the gaze tracking system 200 estimates changes in the gaze direction as if the illumination is always on-axis even when it is not, there may be significant error in the estimation.

For example, 1 mm of misalignment can introduce a couple tens of degrees of error in the gaze direction estimation. However, the amount of error is consistent regardless of the gaze direction. Therefore, the error is highly predictable once the amount of misalignment is determined. Moreover, the relationship between displacements of the pattern and the gaze direction is maintained independent of the misalignments. Any error introduced by misalignment may be included in the equations used to compute the horizontal and vertical displacements.

In one embodiment, misalignment is detected using video-based tracking at a low frame rate. In contrast to the fast movements of the eye, the misalignment of a head-mounted display device happens relatively slowly. In one embodiment, high resolution, but low frame rate conventional video-based tracking is used to quantify the misalignment while on-axis gaze tracking constantly performs fast and low-latency gaze direction estimation.

In one embodiment, misalignment is detected using multiple focii. There is more than one source of reflection in the eye. Individual patterns for each of the reflected light are aligned to form a combined pattern when perfect on-axis illumination is used. However, the individual patterns will be displaced relative to each other if the illumination is misaligned. The relative displacements of the individual patterns may be used to quantify the misalignment.

In one embodiment, misalignment is detected and quantified based on polarization. Light reflected off the retinal surface is polarized and that the polarization is symmetric about the fovea. Thus, the polarization of the reflected pattern indicates which part of the retina is illuminated. The polarization of the pattern may be used to quantify misalignment of the illumination.

Relying on the geometric relationship between the rotational center of the eye and the converging light rays that are directed toward the rotational center 105 of the eye and are reflected along the same path, towards the rotational center 105, enables simple calculations for computing changes in the gaze direction. Therefore, the latency for gaze tracking is reduced and the sampling rate may be increased. Additionally, power consumption is reduced because the complexity of the calculations required to interpret the signals provided by the optical sensor 255 is reduced.

Parallel Processing Architecture

Figure 3:
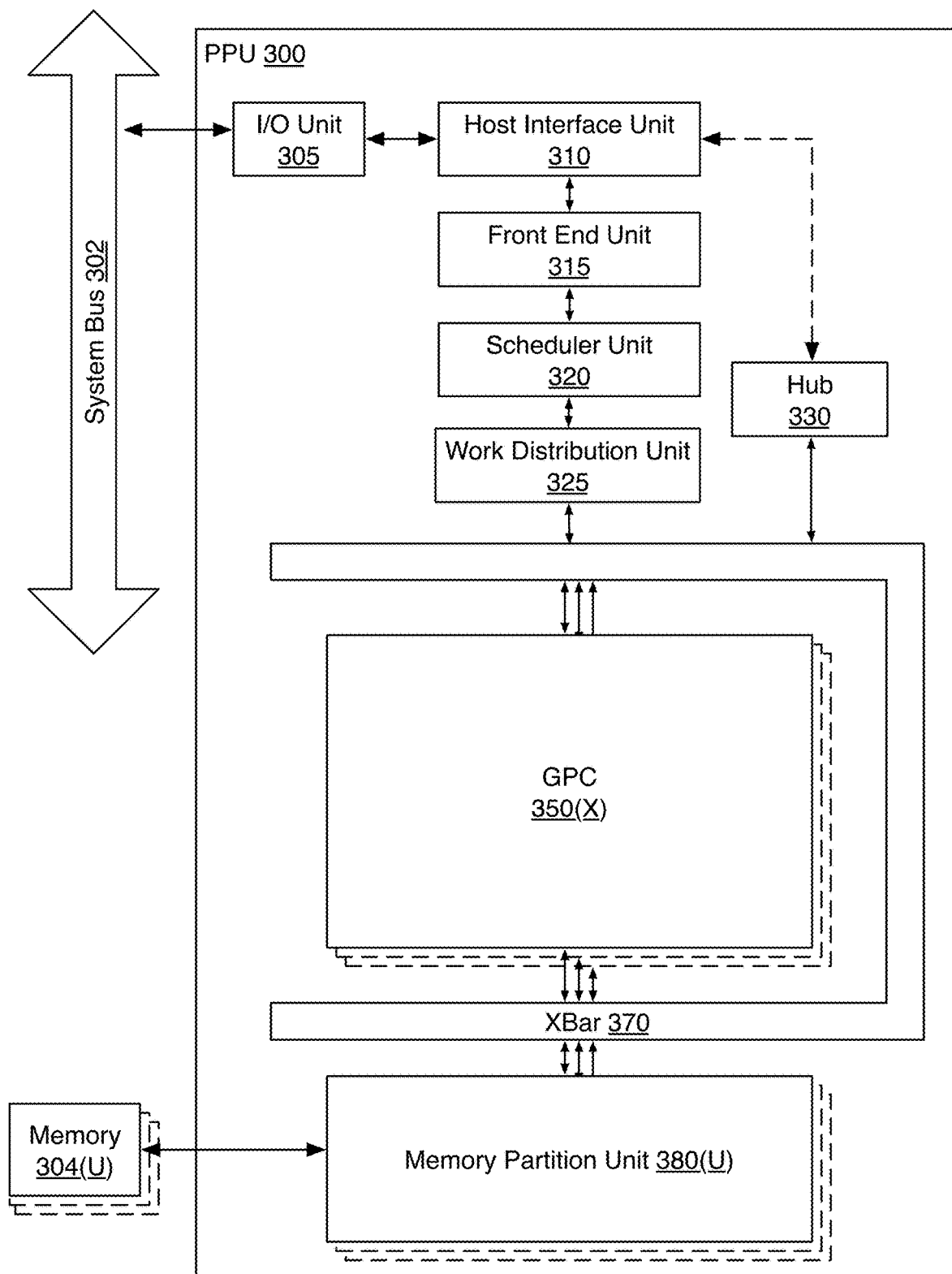
FIG. 3 illustrates a parallel processing unit, in accordance with one embodiment.

FIG. 3 illustrates a parallel processing unit (PPU) 300, in accordance with one embodiment. The PPU 300 may be configured to implement neural network pruning when instructions are executed. In one embodiment, the PPU 300 is configured to implement the neural network pruning system 250.

In one embodiment, the PPU 300 is a multi-threaded processor that is implemented on one or more integrated circuit devices. The PPU 300 is a latency hiding architecture designed to process many threads in parallel. A thread (i.e., a thread of execution) is an instantiation of a set of instructions configured to be executed by the PPU 300. In one embodiment, the PPU 300 is a graphics processing unit (GPU) configured to implement a graphics rendering pipeline for processing three-dimensional (3D) graphics data in order to generate two-dimensional (2D) image data for display on a display device such as a liquid crystal display (LCD) device. In other embodiments, the PPU 300 may be utilized for performing general-purpose computations. While one exemplary parallel processor is provided herein for illustrative purposes, it should be strongly noted that such processor is set forth for illustrative purposes only, and that any processor may be employed to supplement and/or substitute for the same.

As shown in FIG. 3, the PPU 300 includes an Input/Output (I/O) unit 305, a host interface unit 310, a front end unit 315, a scheduler unit 320, a work distribution unit 325, a hub 330, a crossbar (Xbar) 370, one or more general processing clusters (GPCs) 350, and one or more partition units 380. The PPU 300 may be connected to a host processor or other peripheral devices via a system bus 302. The PPU 300 may also be connected to a local memory comprising a number of memory devices 304. In one embodiment, the local memory may comprise a number of dynamic random access memory (DRAM) devices.

The I/O unit 305 is configured to transmit and receive communications (i.e., commands, data, etc.) from a host processor (not shown) over the system bus 302. The I/O unit 305 may communicate with the host processor directly via the system bus 302 or through one or more intermediate devices such as a memory bridge. In one embodiment, the I/O unit 305 implements a Peripheral Component Interconnect Express (PCIe) interface for communications over a PCIe bus. In alternative embodiments, the I/O unit 305 may implement other types of well-known interfaces for communicating with external devices.

The I/O unit 305 is coupled to a host interface unit 310 that decodes packets received via the system bus 302. In one embodiment, the packets represent commands configured to cause the PPU 300 to perform various operations. The host interface unit 310 transmits the decoded commands to various other units of the PPU 300 as the commands may specify. For example, some commands may be transmitted to the front end unit 315. Other commands may be transmitted to the hub 330 or other units of the PPU 300 such as one or more copy engines, a video encoder, a video decoder, a power management unit, etc. (not explicitly shown). In other words, the host interface unit 310 is configured to route communications between and among the various logical units of the PPU 300.

In one embodiment, a program executed by the host processor encodes a command stream in a buffer that provides workloads to the PPU 300 for processing. A workload may comprise several instructions and data to be processed by those instructions. The buffer is a region in a memory that is accessible (i.e., read/write) by both the host processor and the PPU 300. For example, the host interface unit 310 may be configured to access the buffer in a system memory connected to the system bus 302 via memory requests transmitted over the system bus 302 by the I/O unit 305. In one embodiment, the host processor writes the command stream to the buffer and then transmits a pointer to the start of the command stream to the PPU 300. The host interface unit 310 provides the front end unit 315 with pointers to one or more command streams. The front end unit 315 manages the one or more streams, reading commands from the streams and forwarding commands to the various units of the PPU 300.

The front end unit 315 is coupled to a scheduler unit 320 that configures the various GPCs 350 to process tasks defined by the one or more streams. The scheduler unit 320 is configured to track state information related to the various tasks managed by the scheduler unit 320. The state may indicate which GPC 350 a task is assigned to, whether the task is active or inactive, a priority level associated with the task, and so forth. The scheduler unit 320 manages the execution of a plurality of tasks on the one or more GPCs 350.

The scheduler unit 320 is coupled to a work distribution unit 325 that is configured to dispatch tasks for execution on the GPCs 350. The work distribution unit 325 may track a number of scheduled tasks received from the scheduler unit 320. In one embodiment, the work distribution unit 325 manages a pending task pool and an active task pool for each of the GPCs 350. The pending task pool may comprise a number of slots (e.g., 32 slots) that contain tasks assigned to be processed by a particular GPC 350. The active task pool may comprise a number of slots (e.g., 4 slots) for tasks that are actively being processed by the GPCs 350. As a GPC 350 finishes the execution of a task, that task is evicted from the active task pool for the GPC 350 and one of the other tasks from the pending task pool is selected and scheduled for execution on the GPC 350. If an active task has been idle on the GPC 350, such as while waiting for a data dependency to be resolved, then the active task may be evicted from the GPC 350 and returned to the pending task pool while another task in the pending task pool is selected and scheduled for execution on the GPC 350.

The work distribution unit 325 communicates with the one or more GPCs 350 via XBar 370. The XBar 370 is an interconnect network that couples many of the units of the PPU 300 to other units of the PPU 300. For example, the XBar 370 may be configured to couple the work distribution unit 325 to a particular GPC 350. Although not shown explicitly, one or more other units of the PPU 300 are coupled to the host interface unit 310. The other units may also be connected to the XBar 370 via a hub 330.

The tasks are managed by the scheduler unit 320 and dispatched to a GPC 350 by the work distribution unit 325. The GPC 350 is configured to process the task and generate results. The results may be consumed by other tasks within the GPC 350, routed to a different GPC 350 via the XBar 370, or stored in the memory 304. The results can be written to the memory 304 via the partition units 380, which implement a memory interface for reading and writing data to/from the memory 304. In one embodiment, the PPU 300 includes a number U of partition units 380 that is equal to the number of separate and distinct memory devices 304 coupled to the PPU 300. A partition unit 380 will be described in more detail below in conjunction with FIG. 4B.

In one embodiment, a host processor executes a driver kernel that implements an application programming interface (API) that enables one or more applications executing on the host processor to schedule operations for execution on the PPU 300. An application may generate instructions (i.e., API calls) that cause the driver kernel to generate one or more tasks for execution by the PPU 300. The driver kernel outputs tasks to one or more streams being processed by the PPU 300. Each task may comprise one or more groups of related threads, referred to herein as a warp. A thread block may refer to a plurality of groups of threads including instructions to perform the task. Threads in the same group of threads may exchange data through shared memory. In one embodiment, a group of threads comprises 32 related threads.

Figure 4A:
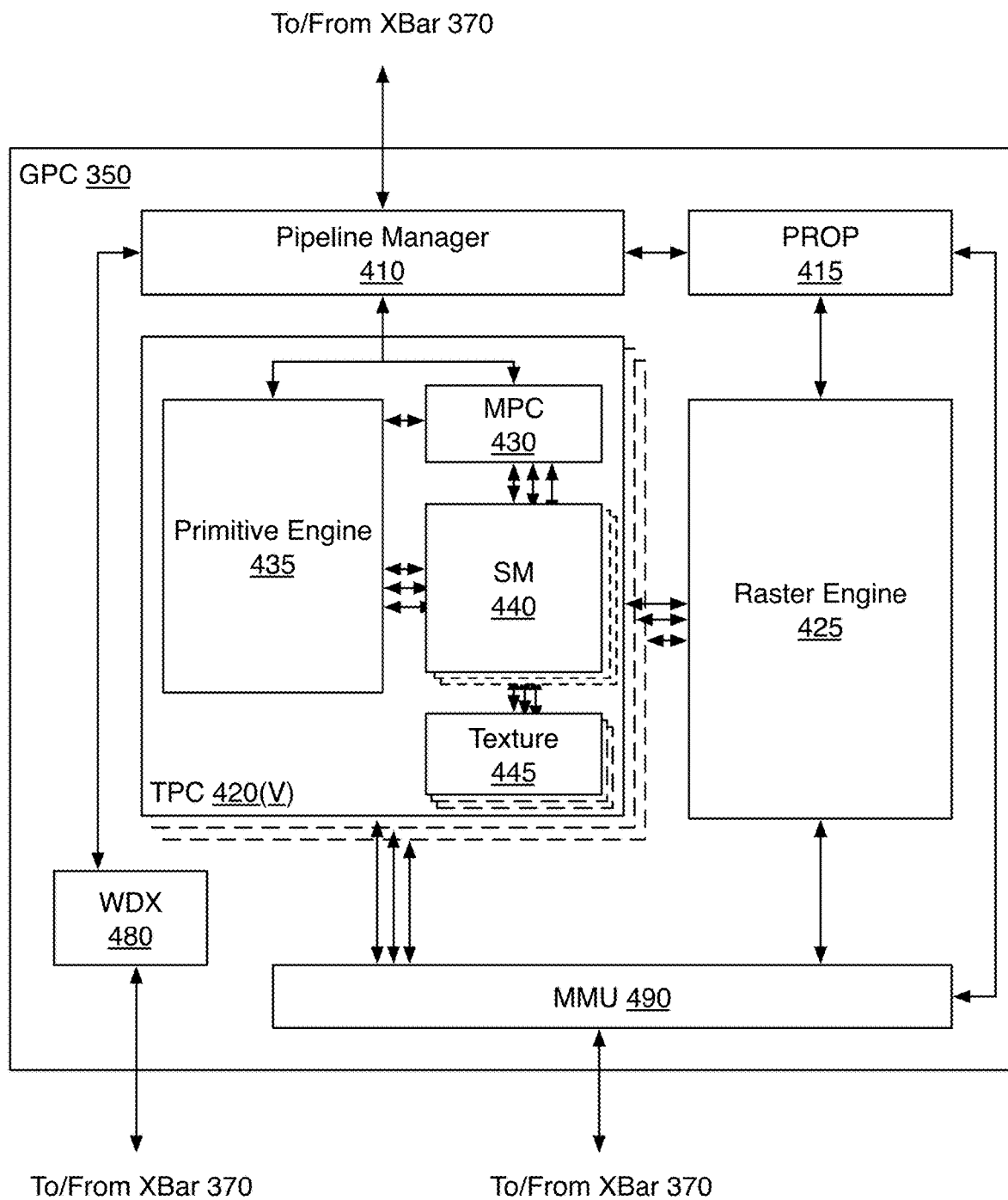
FIG. 4A illustrates a general processing cluster within the parallel processing unit of FIG. 3, in accordance with one embodiment.

FIG. 4A illustrates a GPC 350 within the PPU 300 of FIG. 3, in accordance with one embodiment. As shown in FIG. 4A, each GPC 350 includes a number of hardware units for processing tasks. In one embodiment, each GPC 350 includes a pipeline manager 410, a pre-raster operations unit (PROP) 415, a raster engine 425, a work distribution crossbar (WDX) 480, a memory management unit (MMU) 490, and one or more Texture Processing Clusters (TPCs) 420. It will be appreciated that the GPC 350 of FIG. 4A may include other hardware units in lieu of or in addition to the units shown in FIG. 4A.

In one embodiment, the operation of the GPC 350 is controlled by the pipeline manager 410. The pipeline manager 410 manages the configuration of the one or more TPCs 420 for processing tasks allocated to the GPC 350. In one embodiment, the pipeline manager 410 may configure at least one of the one or more TPCs 420 to implement at least a portion of a graphics rendering pipeline. For example, a TPC 420 may be configured to execute a vertex shader program on the programmable streaming multiprocessor (SM) 440. The pipeline manager 410 may also be configured to route packets received from the work distribution unit 325 to the appropriate logical units within the GPC 350. For example, some packets may be routed to fixed function hardware units in the PROP 415 and/or raster engine 425 while other packets may be routed to the TPCs 420 for processing by the primitive engine 435 or the SM 440.

The PROP unit 415 is configured to route data generated by the raster engine 425 and the TPCs 420 to a Raster Operations (ROP) unit in the partition unit 380, described in more detail below. The PROP unit 415 may also be configured to perform optimizations for color blending, organize pixel data, perform address translations, and the like.

The raster engine 425 includes a number of fixed function hardware units configured to perform various raster operations. In one embodiment, the raster engine 425 includes a setup engine, a coarse raster engine, a culling engine, a clipping engine, a fine raster engine, and a tile coalescing engine. The setup engine receives transformed vertices and generates plane equations associated with the geometric primitive defined by the vertices. The plane equations are transmitted to the coarse raster engine to generate coverage information (e.g., an x,y coverage mask for a tile) for the primitive. The output of the coarse raster engine may be transmitted to the culling engine where fragments associated with the primitive that fail a z-test are culled, and transmitted to a clipping engine where fragments lying outside a viewing frustum are clipped. Those fragments that survive clipping and culling may be passed to a fine raster engine to generate attributes for the pixel fragments based on the plane equations generated by the setup engine. The output of the raster engine 425 comprises fragments to be processed, for example, by a fragment shader implemented within a TPC 420.

Each TPC 420 included in the GPC 350 includes an M-Pipe Controller (MPC) 430, a primitive engine 435, one or more SMs 440, and one or more texture units 445. The MPC 430 controls the operation of the TPC 420, routing packets received from the pipeline manager 410 to the appropriate units in the TPC 420. For example, packets associated with a vertex may be routed to the primitive engine 435, which is configured to fetch vertex attributes associated with the vertex from the memory 304. In contrast, packets associated with a shader program may be transmitted to the SM 440.

In one embodiment, the texture units 445 are configured to load texture maps (e.g., a 2D array of texels) from the memory 304 and sample the texture maps to produce sampled texture values for use in shader programs executed by the SM 440. The texture units 445 implement texture operations such as filtering operations using mip-maps (i.e., texture maps of varying levels of detail). The texture unit 445 is also used as the Load/Store path for SM 440 to MMU 490. In one embodiment, each TPC 420 includes two (2) texture units 445.

The SM 440 comprises a programmable streaming processor that is configured to process tasks represented by a number of threads. Each SM 440 is multi-threaded and configured to execute a plurality of threads (e.g., 32 threads) from a particular group of threads concurrently. In one embodiment, the SM 440 implements a SIMD (Single-Instruction, Multiple-Data) architecture where each thread in a group of threads (i.e., a warp) is configured to process a different set of data based on the same set of instructions. All threads in the group of threads execute the same instructions. In another embodiment, the SM 440 implements a SIMT (Single-Instruction, Multiple Thread) architecture where each thread in a group of threads is configured to process a different set of data based on the same set of instructions, but where individual threads in the group of threads are allowed to diverge during execution. In other words, when an instruction for the group of threads is dispatched for execution, some threads in the group of threads may be active, thereby executing the instruction, while other threads in the group of threads may be inactive, thereby performing a no-operation (NOP) instead of executing the instruction. The SM 440 is described in more detail below in conjunction with FIG. 5.

The MMU 490 provides an interface between the GPC 350 and the partition unit 380. The MMU 490 may provide translation of virtual addresses into physical addresses, memory protection, and arbitration of memory requests. In one embodiment, the MMU 490 provides one or more translation lookaside buffers (TLBs) for performing translation of virtual addresses into physical addresses in the memory 304.

Figure 4B:
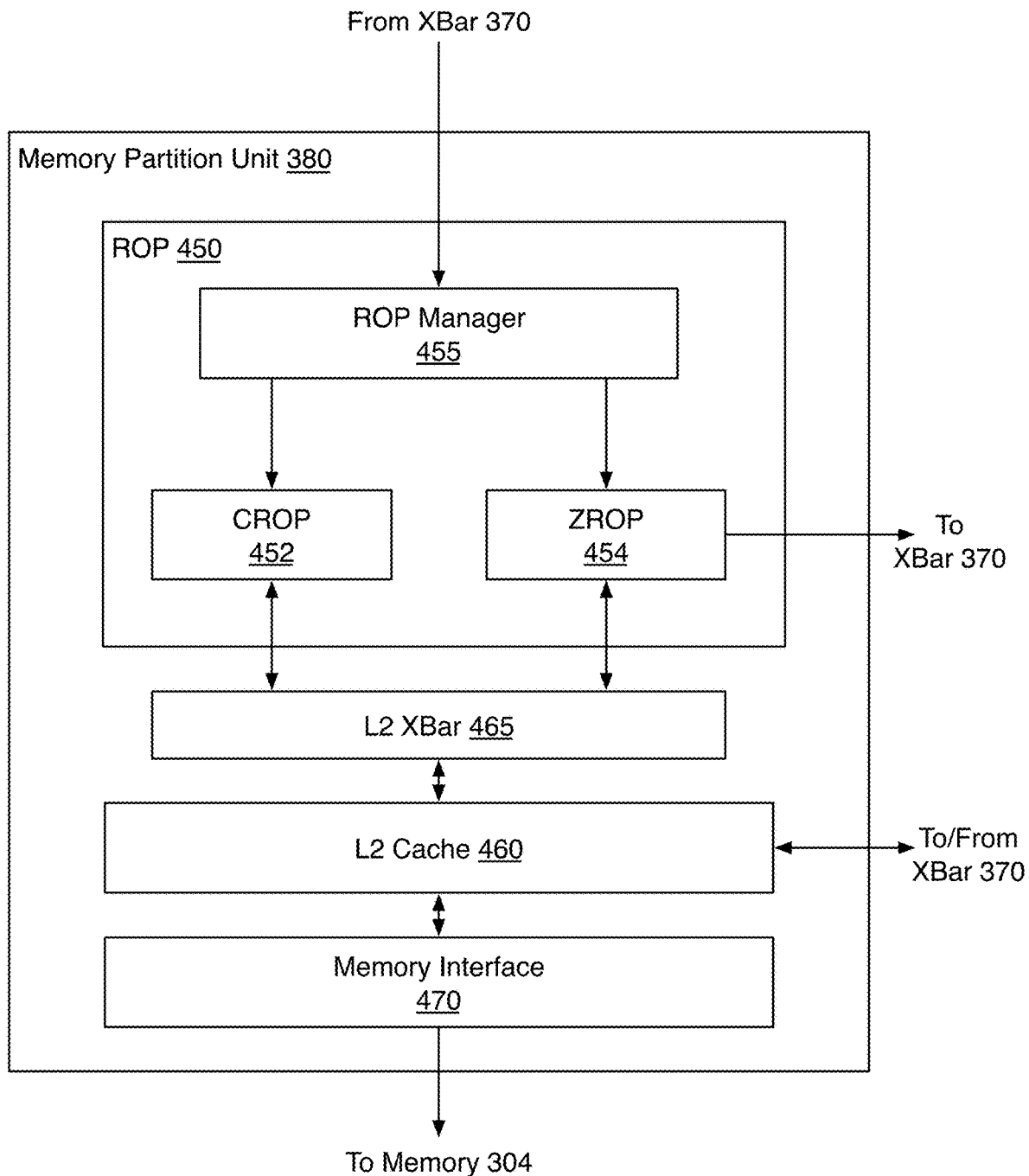
FIG. 4B illustrates a memory partition unit of the parallel processing unit of FIG. 3, in accordance with one embodiment.

FIG. 4B illustrates a memory partition unit 380 of the PPU 300 of FIG. 3, in accordance with one embodiment. As shown in FIG. 4B, the memory partition unit 380 includes a Raster Operations (ROP) unit 450, a level two (L2) cache 460, a memory interface 470, and an L2 crossbar (XBar) 465. The memory interface 470 is coupled to the memory 304. Memory interface 470 may implement 16, 32, 64, 128-bit data buses, or the like, for high-speed data transfer. In one embodiment, the PPU 300 incorporates U memory interfaces 470, one memory interface 470 per partition unit 380, where each partition unit 380 is connected to a corresponding memory device 304. For example, PPU 300 may be connected to up to U memory devices 304, such as graphics double-data-rate, version 5, synchronous dynamic random access memory (GDDR5 SDRAM). In one embodiment, the memory interface 470 implements a DRAM interface and U is equal to 8.

In one embodiment, the PPU 300 implements a multi-level memory hierarchy. The memory 304 is located off-chip in SDRAM coupled to the PPU 300. Data from the memory 304 may be fetched and stored in the L2 cache 460, which is located on-chip and is shared between the various GPCs 350. As shown, each partition unit 380 includes a portion of the L2 cache 460 associated with a corresponding memory device 304. Lower level caches may then be implemented in various units within the GPCs 350. For example, each of the SMs 440 may implement a level one (L1) cache. The L1 cache is private memory that is dedicated to a particular SM 440. Data from the L2 cache 460 may be fetched and stored in each of the L1 caches for processing in the functional units of the SMs 440. The L2 cache 460 is coupled to the memory interface 470 and the XBar 370.

The ROP unit 450 includes a ROP Manager 455, a Color ROP (CROP) unit 452, and a Z ROP (ZROP) unit 454. The CROP unit 452 performs raster operations related to pixel color, such as color compression, pixel blending, and the like. The ZROP unit 454 implements depth testing in conjunction with the raster engine 425. The ZROP unit 454 receives a depth for a sample location associated with a pixel fragment from the culling engine of the raster engine 425. The ZROP unit 454 tests the depth against a corresponding depth in a depth buffer for a sample location associated with the fragment. If the fragment passes the depth test for the sample location, then the ZROP unit 454 updates the depth buffer and transmits a result of the depth test to the raster engine 425. The ROP Manager 455 controls the operation of the ROP unit 450. It will be appreciated that the number of partition units 380 may be different than the number of GPCs 350 and, therefore, each ROP unit 450 may be coupled to each of the GPCs 350. Therefore, the ROP Manager 455 tracks packets received from the different GPCs 350 and determines which GPC 350 that a result generated by the ROP unit 450 is routed to. The CROP unit 452 and the ZROP unit 454 are coupled to the L2 cache 460 via an L2 XBar 465.

Figure 5:
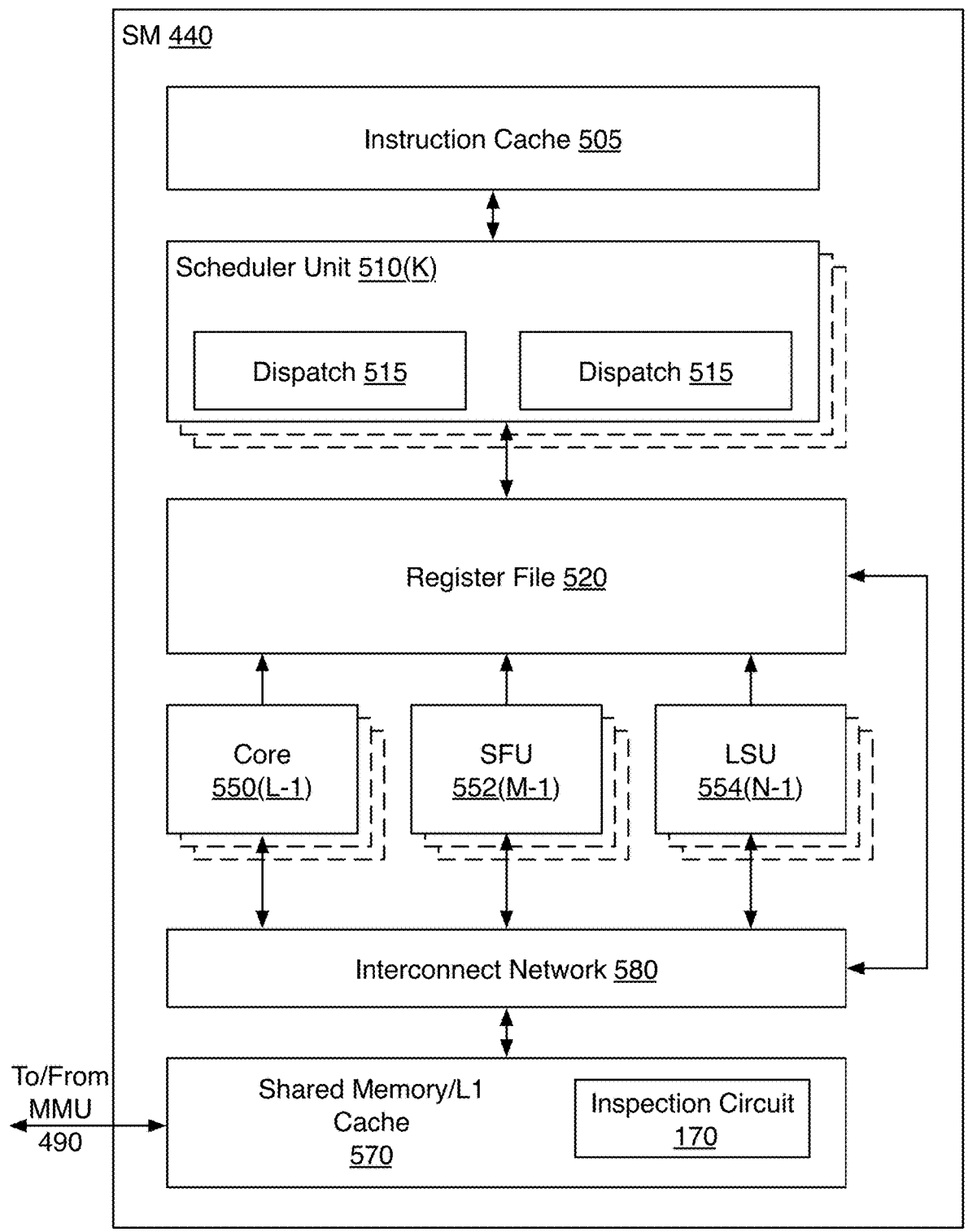
FIG. 5 illustrates the streaming multi-processor of FIG. 4A, in accordance with one embodiment.

FIG. 5 illustrates the streaming multi-processor 440 of FIG. 4A, in accordance with one embodiment. As shown in FIG. 5, the SM 440 includes an instruction cache 505, one or more scheduler units 510, a register file 520, one or more processing cores 550, one or more special function units (SFUs) 552, one or more load/store units (LSUs) 554, an interconnect network 580, a shared memory/L1 cache 570. In one embodiment, the instruction cache 105, the load/store unit 154, and the register file 115, shown in FIG. 1B is the instruction cache 505, the load/store unit (LSU) 554, and the register file 520, respectively.

As described above, the work distribution unit 325 dispatches tasks for execution on the GPCs 350 of the PPU 300. The tasks are allocated to a particular TPC 420 within a GPC 350 and, if the task is associated with a shader program, the task may be allocated to an SM 440. The scheduler unit 510 receives the tasks from the work distribution unit 325 and manages instruction scheduling for one or more groups of threads (i.e., warps) assigned to the SM 440. The scheduler unit 510 schedules threads for execution in groups of parallel threads, where each group is called a warp. In one embodiment, each warp includes 32 threads. The scheduler unit 510 may manage a plurality of different warps, scheduling the warps for execution and then dispatching instructions from the plurality of different warps to the various functional units (i.e., cores 550, SFUs 552, and LSUs 554) during each clock cycle.

Each dispatch unit 515 is configured to transmit instructions to one or more of the functional units. In the embodiment shown in FIG. 5, the scheduler unit 510 includes two dispatch units 515 that enable two different instructions from the same warp to be dispatched during each clock cycle. In alternative embodiments, each scheduler unit 510 may include a single dispatch unit 515 or additional dispatch units 515.

Each SM 440 includes a register file 520 that provides a set of registers for the functional units of the SM 440. In one embodiment, the register file 520 is divided between each of the functional units such that each functional unit is allocated a dedicated portion of the register file 520. In another embodiment, the register file 520 is divided between the different warps being executed by the SM 440. The register file 520 provides temporary storage for operands connected to the data paths of the functional units.

Each SM 440 comprises L processing cores 550. In one embodiment, the SM 440 includes a large number (e.g., 128, etc.) of distinct processing cores 550. Each core 550 may include a fully-pipelined, single-precision processing unit that includes a floating point arithmetic logic unit and an integer arithmetic logic unit. The core 550 may also include a double-precision processing unit including a floating point arithmetic logic unit. In one embodiment, the floating point arithmetic logic units implement the IEEE 754-2008 standard for floating point arithmetic. Each SM 440 also comprises M SFUs 552 that perform special functions (e.g., attribute evaluation, reciprocal square root, and the like), and N LSUs 554 that implement load and store operations between the shared memory/L1 cache 570 and the register file 520. In one embodiment, the SM 440 includes 128 cores 550, 32 SFUs 552, and 32 LSUs 554.

Each SM 440 includes an interconnect network 580 that connects each of the functional units to the register file 520 and the LSU 554 to the register file 520, shared memory/L1 cache 570. In one embodiment, the interconnect network 580 is a crossbar that can be configured to connect any of the functional units to any of the registers in the register file 520 and connect the LSUs 554 to the register file and memory locations in shared memory/L1 cache 570.

The shared memory/L1 cache 570 is an array of on-chip memory that allows for data storage and communication between the SM 440 and the primitive engine 435 and between threads in the SM 440. In one embodiment, the shared memory/L1 cache 570 comprises 64 KB of storage capacity and is in the path from the SM 440 to the partition unit 380. The shared memory/L1 cache 570 can be used to cache reads and writes. In one embodiment, the shared memory/L1 cache 570 includes the inspection circuit 170 to perform inline data inspection for load operations. In one embodiment, at least one inspection circuit 170 is positioned between the shared memory/L1 cache 570 and the LSUs 554.

The PPU 300 described above may be configured to perform highly parallel computations much faster than conventional CPUs. Parallel computing has advantages in graphics processing, data compression, neural networks, deep learning, biometrics, stream processing algorithms, and the like.

When configured for general purpose parallel computation, a simpler configuration can be used. In this model, as shown in FIG. 3, fixed function graphics processing units are bypassed, creating a much simpler programming model. In this configuration, the work distribution unit 325 assigns and distributes blocks of threads directly to the TPCs 420. The threads in a block execute the same program, using a unique thread ID in the calculation to ensure each thread generates unique results, using the SM 440 to execute the program and perform calculations, shared memory/L1 cache 570 to communicate between threads, and the LSU 554 to read and write Global memory through partition shared memory/L1 cache 570 and partition unit 380. When configured for general purpose parallel computation, the SM 440 can also write commands that scheduler unit 320 can use to launch new work on the TPCs 420.

In one embodiment, the PPU 300 comprises a deep learning or machine learning processor. The PPU 300 is configured to receive commands that specify programs for modeling neural networks and processing data according to a neural network.

In one embodiment, the PPU 300 comprises a graphics processing unit (GPU). The PPU 300 is configured to receive commands that specify shader programs for processing graphics data. Graphics data may be defined as a set of primitives such as points, lines, triangles, quads, triangle strips, and the like. Typically, a primitive includes data that specifies a number of vertices for the primitive (e.g., in a model-space coordinate system) as well as attributes associated with each vertex of the primitive. The PPU 300 can be configured to process the graphics primitives to generate a frame buffer (i.e., pixel data for each of the pixels of the display).

An application writes model data for a scene (i.e., a collection of vertices and attributes) to a memory such as a system memory or memory 304. The model data defines each of the objects that may be visible on a display. The application then makes an API call to the driver kernel that requests the model data to be rendered and displayed. The driver kernel reads the model data and writes commands to the one or more streams to perform operations to process the model data. The commands may reference different shader programs to be implemented on the SMs 440 of the PPU 300 including one or more of a vertex shader, hull shader, domain shader, geometry shader, and a pixel shader. For example, one or more of the SMs 440 may be configured to execute a vertex shader program that processes a number of vertices defined by the model data. In one embodiment, the different SMs 440 may be configured to execute different shader programs concurrently. For example, a first subset of SMs 440 may be configured to execute a vertex shader program while a second subset of SMs 440 may be configured to execute a pixel shader program. The first subset of SMs 440 processes vertex data to produce processed vertex data and writes the processed vertex data to the L2 cache 460 and/or the memory 304. After the processed vertex data is rasterized (i.e., transformed from three-dimensional data into two-dimensional data in screen space) to produce fragment data, the second subset of SMs 440 executes a pixel shader to produce processed fragment data, which is then blended with other processed fragment data and written to the frame buffer in memory 304. The vertex shader program and pixel shader program may execute concurrently, processing different data from the same scene in a pipelined fashion until all of the model data for the scene has been rendered to the frame buffer. Then, the contents of the frame buffer are transmitted to a display controller for display on a display device.

The PPU 300 may be included in a desktop computer, a laptop computer, a tablet computer, a smart-phone (e.g., a wireless, hand-held device), personal digital assistant (PDA), a digital camera, a hand-held electronic device, and the like. In one embodiment, the PPU 300 is embodied on a single semiconductor substrate. In another embodiment, the PPU 300 is included in a system-on-a-chip (SoC) along with one or more other logic units such as a reduced instruction set computer (RISC) CPU, a memory management unit (MMU), a digital-to-analog converter (DAC), and the like.

In one embodiment, the PPU 300 may be included on a graphics card that includes one or more memory devices 304 such as GDDR5 SDRAM. The graphics card may be configured to interface with a PCIe slot on a motherboard of a desktop computer that includes, e.g., a northbridge chipset and a southbridge chipset. In yet another embodiment, the PPU 300 may be an integrated graphics processing unit (iGPU) included in the chipset (i.e., Northbridge) of the motherboard.

Various programs may be executed within the PPU 300 in order to implement the various layers of a neural network. For example, the device driver may launch a kernel on the PPU 300 to implement the neural network on one SM 440 (or multiple SMs 440). The device driver (or the initial kernel executed by the PPU 300) may also launch other kernels on the PPU 300 to perform other layers of the neural network. In addition, some of the layers of the neural network may be implemented on fixed unit hardware implemented within the PPU 300. It will be appreciated that results from one kernel may be processed by one or more intervening fixed function hardware units before being processed by a subsequent kernel on an SM 440.

Exemplary System

Figure 6:
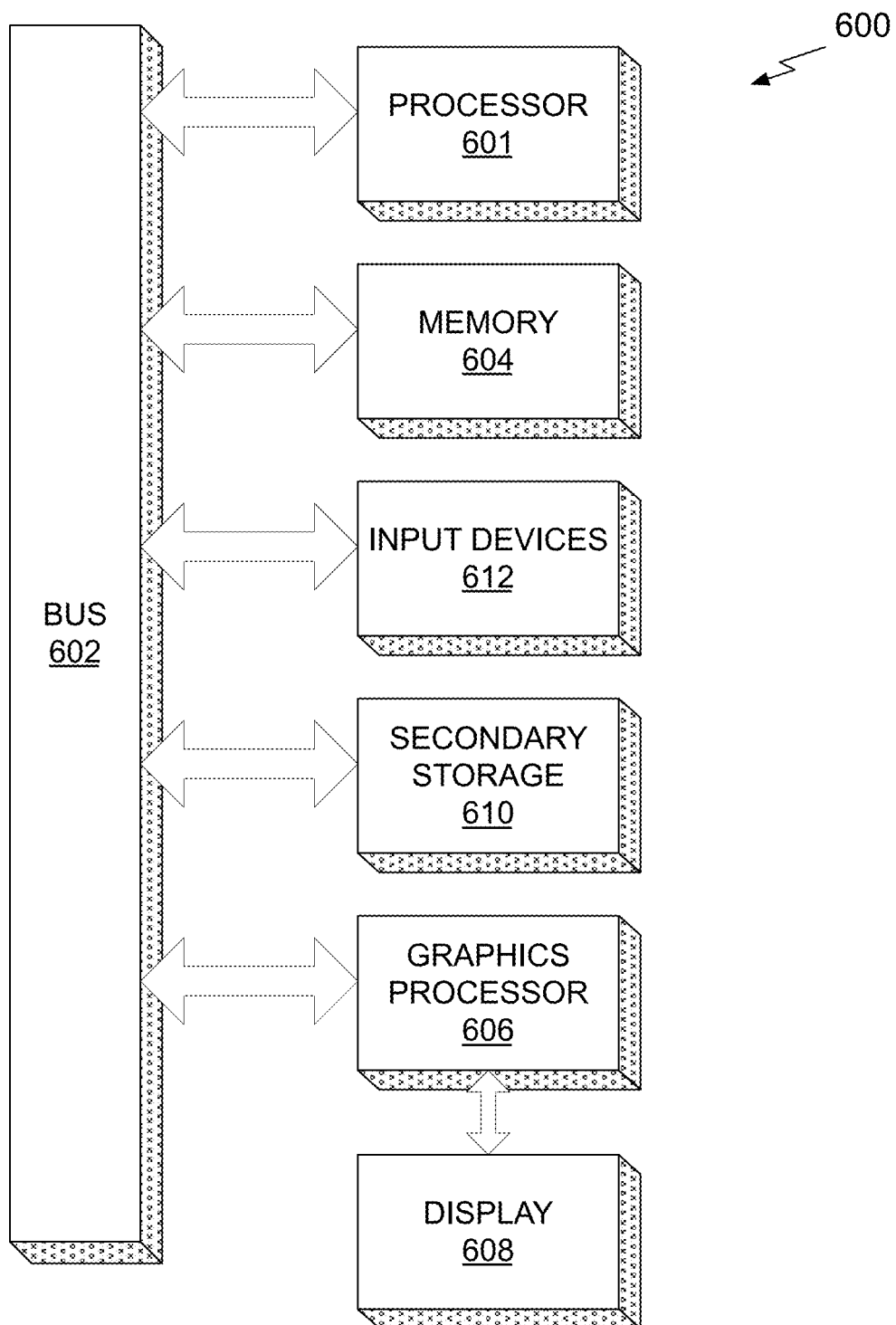
FIG. 6 illustrates an exemplary system in which the various architecture and/or functionality of the various previous embodiments may be implemented.

FIG. 6 illustrates an exemplary system 600 in which the various architecture and/or functionality of the various previous embodiments may be implemented.

As shown, a system 600 is provided including at least one central processor 601 that is connected to a communication bus 602. The communication bus 602 may be implemented using any suitable protocol, such as PCI (Peripheral Component Interconnect), PCI-Express, AGP (Accelerated Graphics Port), HyperTransport, or any other bus or point-to-point communication protocol(s). In one embodiment, the communication bus 602 is the system bus 302 shown in FIG. 3. The system 600 also includes a main memory 604. Control logic (software) and data are stored in the main memory 604 which may take the form of random access memory (RAM).

The system 600 also includes input devices 612, a graphics processor 606, and a display 608, i.e. a conventional CRT (cathode ray tube), LCD (liquid crystal display), LED (light emitting diode), plasma display or the like. User input may be received from the input devices 612, e.g., keyboard, mouse, touchpad, microphone, and the like. In one embodiment, the graphics processor 606 may include a plurality of shader modules, a rasterization module, etc. Each of the foregoing modules may even be situated on a single semiconductor platform to form a graphics processing unit (GPU).

In the present description, a single semiconductor platform may refer to a sole unitary semiconductor-based integrated circuit or chip. It should be noted that the term single semiconductor platform may also refer to multi-chip modules with increased connectivity which simulate on-chip operation, and make substantial improvements over utilizing a conventional central processing unit (CPU) and bus implementation. Of course, the various modules may also be situated separately or in various combinations of semiconductor platforms per the desires of the user.

The system 600 may also include a secondary storage 610. The secondary storage 610 includes, for example, a hard disk drive and/or a removable storage drive, representing a floppy disk drive, a magnetic tape drive, a compact disk drive, digital versatile disk (DVD) drive, recording device, universal serial bus (USB) flash memory. The removable storage drive reads from and/or writes to a removable storage unit in a well-known manner.

Computer programs, or computer control logic algorithms, may be stored in the main memory 604 and/or the secondary storage 610. Such computer programs, when executed, enable the system 600 to perform various functions. The memory 604, the storage 610, and/or any other storage are possible examples of computer-readable media.

In one embodiment, the architecture and/or functionality of the various previous figures may be implemented in the context of the central processor 601, the graphics processor 606, an integrated circuit (not shown) that is capable of at least a portion of the capabilities of both the central processor 601 and the graphics processor 606, a chipset (i.e., a group of integrated circuits designed to work and sold as a unit for performing related functions, etc.), and/or any other integrated circuit for that matter.

Still yet, the architecture and/or functionality of the various previous figures may be implemented in the context of a general computer system, a circuit board system, a game console system dedicated for entertainment purposes, an application-specific system, and/or any other desired system. For example, the system 600 may take the form of an autonomous vehicle, desktop computer, laptop computer, server, workstation, game console, embedded system, and/or any other type of logic. Still yet, the system 600 may take the form of various other devices including, but not limited to a personal digital assistant (PDA) device, a mobile phone device, head-mounted display, a television, etc.

Further, while not shown, the system 600 may be coupled to a network (e.g., a telecommunications network, local area network (LAN), wireless network, wide area network (WAN) such as the Internet, peer-to-peer network, cable network, or the like) for communication purposes.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A gaze tracking system, comprising:
   an optical sensor configured to:
      receive reflected light rays produced by light rays that converge toward a rotational center of an eye and are reflected by one or more optical components of the eye toward the optical sensor, and
      generate pattern data based on intersections of the reflected light rays at a surface of the optical sensor, wherein the optical sensor is a quadrant photo detector and the pattern data includes an illumination intensity value corresponding to each quadrant of the quadrant photo detector; and
   a processor configured to compute an estimated gaze direction of the eye based on the pattern data by calculating a displacement based on the illumination intensity value for each quadrant.

2. The gaze tracking system of claim 1, wherein at least a portion of the reflected light rays reflect off a retina of the eye.

3. The gaze tracking system of claim 1, wherein at least a portion of the reflected light rays reflect off a cornea or a crystalline lens of the eye.

4. The gaze tracking system of claim 1, wherein computing the estimated gaze direction comprises:
   computing a horizontal displacement based on the illumination intensity values according to the following equation:

$$\frac{[(Q2+Q3)-(Q1+Q4)]}{[(Q2+Q3)+(Q1+Q4)]};$$

computing a vertical displacement based on the illumination intensity values according to the following equation:

$$\frac{[(Q1+Q2)-(Q3+Q4)]}{[(Q1+Q2)+(Q3+Q4)]}; \text{ and}$$

mapping the horizontal displacement and the vertical displacement to a position within a display, wherein Q1 is an illumination intensity value for a first quadrant of the quadrant photo detector, Q2 is an illumination intensity value for a second quadrant of the quadrant photo detector, Q3 is an illumination intensity value for a third quadrant of the quadrant photo detector, and Q4 is an illumination intensity value for a fourth quadrant of the quadrant photo detector.

5. The gaze tracking system of claim 1, further comprising an adjustable mirror configured to direct the reflected light rays along a path to reach the optical sensor, wherein computing the estimated gaze direction comprises:

adjusting a steering angle of the adjustable mirror relative to the optical detector to center the pattern data at the surface of the optical detector; and computing a position within a display based on the steering angle.

6. The gaze tracking system of claim 1, further comprising an optical element configured to direct the reflected light rays from the eye along a path to reach the optical sensor.

7. The gaze tracking system of claim 6, wherein the optical element is a holographic optical element.

8. The gaze tracking system of claim 6, wherein the optical element is a beam splitter.

9. The gaze tracking system of claim 1, wherein the reflected light rays include retro-reflected light rays.

10. The gaze tracking system of claim 1, further comprising measuring a gaze direction error produced by a misalignment between an original orientation between the eye and the optical sensor and a current orientation between the eye and the optical sensor, wherein the processor is further configured to compute the estimated gaze direction of the eye based on the gaze direction error.

11. A computer-implemented method, comprising:
receiving reflected light rays at an optical sensor, wherein light rays produced by a light source converge towards a rotational center of an eye and are reflected by one or more optical components of the eye toward the optical sensor as the reflected light rays; and generating pattern data based on intersections of the reflected light rays at a surface of the optical sensor, wherein the optical sensor is a quadrant photo detector and the pattern data includes an illumination intensity value corresponding to each quadrant of the quadrant photo detector; and computing, by a processor, an estimated gaze direction of the eye based on the pattern data by calculating a displacement based on the illumination intensity value for each quadrant.

12. The computer-implemented method of claim 11, wherein at least a portion of the reflected light rays reflect off a retina of the eye.

13. The computer-implemented method of claim 11, wherein at least a portion of the reflected light rays reflect off a cornea or a crystalline lens of the eye.

14. The computer-implemented method of claim 11, wherein computing the estimated gaze direction comprises:
computing a horizontal displacement based on the illumination intensity values according to the following equation:

$$\frac{[(Q2+Q3)-(Q1+Q4)]}{[(Q2+Q3)+(Q1+Q4)]};$$

computing a vertical displacement based on the illumination intensity values according to the following equation:

$$\frac{[(Q1+Q2)-(Q3+Q4)]}{[(Q1+Q2)+(Q3+Q4)]}; \text{ and}$$

mapping the horizontal displacement and the vertical displacement to a position within a display, wherein Q1 is an illumination intensity value for a first quadrant of the quadrant photo detector, Q2 is an illumination intensity value for a second quadrant of the quadrant photo detector, Q3 is an illumination intensity value for a third quadrant of the quadrant photo detector, and Q4 is an illumination intensity value for a fourth quadrant of the quadrant photo detector.

15. A non-transitory, computer-readable storage medium storing instructions that, when executed by a processor, cause the processor to perform steps comprising:
generating pattern data based on intersections of reflected light rays at a surface of an optical sensor, wherein light rays produced by a light source converge towards a rotational center of an eye and are reflected by one or more optical components of the eye toward the optical sensor as the reflected light rays, wherein the optical sensor is a quadrant photo detector and the pattern data includes an illumination intensity value corresponding to each quadrant of the quadrant photo detector; and computing an estimated gaze direction of the eye based on the pattern data by calculating a displacement based on the illumination intensity value for each quadrant.

* * * * *